US007181966B2

(12) United States Patent
Isogai et al.

(10) Patent No.: US 7,181,966 B2
(45) Date of Patent: Feb. 27, 2007

(54) PHYSICAL QUANTITY SENSOR AND METHOD FOR MANUFACTURING THE SAME

(75) Inventors: Toshiki Isogai, Nagoya (JP); Masato Ishihara, Anjo (JP); Michitaka Hayashi, Nagoya (JP); Toshikazu Itakura, Toyota (JP)

(73) Assignees: Nippon Soken, Inc., Nishio (JP); Denso Corporation, Kariya (JP)

( * ) Notice: Subject to any disclaimer, the term of this patent is extended or adjusted under 35 U.S.C. 154(b) by 0 days.

(21) Appl. No.: 11/220,543

(22) Filed: Sep. 8, 2005

(65) Prior Publication Data

US 2006/0048572 A1    Mar. 9, 2006

(30) Foreign Application Priority Data

| Sep. 8, 2004 | (JP) | ............................. 2004-261423 |
| Sep. 14, 2004 | (JP) | ............................. 2004-267204 |
| Sep. 14, 2004 | (JP) | ............................. 2004-267205 |
| Sep. 29, 2004 | (JP) | ............................. 2004-284410 |

(51) Int. Cl.
G01N 19/10 (2006.01)
G01N 27/22 (2006.01)
G11C 8/10 (2006.01)

(52) U.S. Cl. ................. 73/335.04; 73/29.02; 73/29.05; 73/335.02; 326/105; 326/108; 361/301.1; 361/303; 361/329

(58) Field of Classification Search ............... 73/29.01, 73/29.02, 29.05, 335.01–335.05; 326/105, 326/106, 108; 361/301.1, 303, 311, 313, 361/329

See application file for complete search history.

(56) References Cited

U.S. PATENT DOCUMENTS

| 3,617,830 | A | * | 11/1971 | Perna, Jr. ..................... 361/329 |
| 4,144,636 | A | * | 3/1979 | Burkhardt et al. ............ 438/49 |
| 4,881,199 | A | * | 11/1989 | Kowalski ............... 365/185.25 |
| 6,445,565 | B1 | | 9/2002 | Toyoda et al. |
| 6,566,893 | B2 | | 5/2003 | Kiesewetter et al. |
| 6,580,600 | B2 | | 6/2003 | Toyoda et al. |
| 6,628,501 | B2 | * | 9/2003 | Toyoda ........................ 361/303 |
| 6,690,569 | B1 | * | 2/2004 | Mayer et al. ................ 361/303 |
| 6,834,547 | B2 | * | 12/2004 | Chen et al. ............... 73/335.02 |
| 6,882,165 | B2 | * | 4/2005 | Ogura ......................... 324/663 |
| 2002/0109959 | A1 | * | 8/2002 | Toyoda et al. .............. 361/311 |
| 2002/0114125 | A1 | | 8/2002 | Toyoda et al. |
| 2004/0254306 | A1 | | 12/2004 | Isogai et al. |

FOREIGN PATENT DOCUMENTS

JP    A-56-74992    6/1981

(Continued)

*Primary Examiner*—Hezron Williams
*Assistant Examiner*—David A. Rogers
(74) *Attorney, Agent, or Firm*—Posz Law Group, PLC

(57) ABSTRACT

A capacitance type humidity sensor includes: a detection substrate including a detection portion on a first side of the detection substrate; and a circuit board including a circuit portion. The detection portion detects humidity on the basis of capacitance change of the detection portion. The circuit portion processes the capacitance change as an electric signal. The detection substrate further includes a sensor pad on a second side of the detection substrate. The sensor pad is electrically connected to the detection portion through a conductor in a through hole of the detection substrate.

6 Claims, 12 Drawing Sheets

FOREIGN PATENT DOCUMENTS

| | | |
|---|---|---|
| JP | A-60-147643 | 8/1985 |
| JP | U-61-26162 | 2/1986 |
| JP | A-62-182643 | 8/1987 |
| JP | U-2-140351 | 11/1990 |
| JP | A-3-109800 | 5/1991 |
| JP | A-4-346492 | 12/1992 |
| JP | A-5-114710 | 5/1993 |
| JP | A-6-58900 | 3/1994 |
| JP | A-9-27665 | 1/1997 |
| JP | A-10-84184 | 3/1998 |

* cited by examiner

PHYSICAL QUANTITY SENSOR AND METHOD FOR MANUFACTURING THE SAME

CROSS REFERENCE TO RELATED APPLICATIONS

This application is based on Japanese Patent Applications No. 2004-261423 filed on Sep. 8, 2004, No. 2004-267204 filed on Sep. 14, 2004, No. 2004-267205 filed on Sep. 14, 2004, and No. 2004-284410 filed on Sep. 29, 2004, the disclosures of which are incorporated herein by reference.

FIELD OF THE INVENTION

The present invention relates to a physical quantity sensor and a method for manufacturing a physical quantity sensor.

BACKGROUND OF THE INVENTION

As one of conventional capacitance type humidity sensors as a physical quantity sensor manufactured by interposing a humidity sensitive film whose relative dielectric constant is changed in response to humidity between one pair of electrodes. This type of sensor is disclosed in, for example, Japanese Laid-open Patent Application No. 2002-243690, which corresponds to U.S. Pat. No. 6,580,600 and US 2002-0114125A1.

The capacitance type humidity sensor has been manufactured by that one pair of electrodes are formed in such a manner that the one-paired electrodes are separated from each other and are located opposite to each other on the same plane of a semiconductor substrate, and a humidity sensitive film is formed on the semiconductor substrate in such a manner that the humidity sensitive film covers the one-paired electrodes, and a space between the one-pared electrodes. The relative dielectric constant of the humidity sensitive film is changed in response to humidity. Also, while an insulating film (second insulating film) has been formed between the electrodes and the humidity sensitive film, a humidity resistive characteristic as to the electrodes may be secured by this insulating film. As a consequence, even if an expensive metal having a superior humidity resistive characteristic such as a noble metal is not especially used, these electrodes can be manufactured by employing such a material, for instance, aluminum (i.e., Al), which can be used in a normal semiconductor manufacturing line.

Also, a circuit unit (circuit element unit) for processing a capacitance change between the electrodes so as to obtain an electric signal has been provided on the side of a plane of a semiconductor substrate, on which the electrodes are formed. If a wiring material employed in this circuit unit is the same as the structural material of the electrodes, then manufacturing steps may be made simple.

On the other hand, in the capacitance type humidity sensor having the above-described structure, in order to protect pads (namely, to prevent corrosion) which may function as external connection terminals provided at least on an edge portion of the circuit unit, surfaces of these pads must be covered by such a protecting material as gel, or the like.

However, both the electrodes and the circuit unit have been formed in an integrated manner on the same plane side of the semiconductor substrate. Also, it is practically difficult to locally coat the gel. As a consequence, the entire surface of the circuit forming plane of the semiconductor substrate is covered by the gel, and the upper portion of the detecting unit made of both the electrodes and the humidity sensitive film is also covered by the gel, so that the response characteristic of the capacitance type humidity sensor is deteriorated.

Also, other than the above-explained structure, another capacitance type humidity sensor having the following structure is known. That is, while a detection board having a detecting unit whose capacitance is changed by humidity and a circuit board having a circuit unit are separately prepared, sensor pads electrically connected to electrodes via a bonding wire, or the like, are electrically connected to the circuit units in this capacitance type humidity sensor. However, also, in this case, since the sensor pads of the detection board must be covered, both the humidity sensitive film and the upper portion of the electrodes are covered by the gel, so that the response characteristic of the capacitance type humidity sensor is deteriorated.

The above capacitance type humidity sensor has been manufactured by that one pair of electrodes are formed in such a manner that the one-paired electrodes are separated from each other and are located opposite to each other on the same plane of a substrate, and a humidity sensitive film is formed on the substrate in such a manner that the humidity sensitive film covers the one-paired electrodes, and a space between the one-pared electrodes. The relative dielectric constant of the humidity sensitive film is changed in response to humidity.

In this case, in a manufacturing operation of the above-described capacitance type humidity sensor, if paste containing a polymer material corresponding to a structural material is screen-printed, and then, the printed paste is hardened so as to form a humidity forming film, then a patterning process by a photo-process required in such a case that a spin coat method is applied can be eliminated. In other words, the manufacturing steps can be simplified. Also, there is another merit that the apparatus can be easily handled.

On the other hand, in the screen printing operation, since the paste is printed on the substrate via the pattern holes formed in the screen mask, the screen mask must be correctly positioned with respect to the substrate. Also, in the above-explained capacitance type humidity sensor, the high positioning precision of the humidity sensitive film is necessarily required in connection with, especially, the compactness of the sensor build, so that the screen mask must be correctly positioned with respect to the substrate.

To this end, conventionally, when a screen mask is positioned with respect to a substrate, for example, the screen mask abuts against a dummy substrate (namely, test-purpose substrate) and paste is screen-printed. Then, a position of a printing area which has been printed through pattern holes is detected by employing an imaging apparatus such as a CCD camera. Then, the substrate is positioned on a stage in order that the detected printing area and the area which is wanted to be printed may become substantially same positions. Under this positioning condition, a printing operation is carried out.

However, in the case of screen printing operations, it is practically difficult to uniform thicknesses of humidity sensitive films. This reason is caused by that, for instance, a so-called "saddle" phenomenon occurs in edge areas. As a consequence, in order that effective areas of center portions (which are surrounded by edge portions) whose film thicknesses become substantially uniform are arranged in such areas on substrates, which are wanted to be printed, pattern holes have been set to be larger than the areas which are wanted to be printed. Also, in the case of screen printing operations, since squeezes are slid so as to print paste, shapes and/or dimensions of areas (humidity sensitive films) which have been actually printed are more or less different from pattern holes. In other words, there are large differences in the shapes and/or dimensions between the area on the substrate which is wanted to be printed, and the area which has been actually printed on the dummy substrate. Thus, even when the positioning operation of the substrate is carried out while the printed area is employed as the reference area, there is such a problem that the humidity sensitive film cannot be formed in high positioning precision.

The above capacitance type humidity sensor has been manufactured by comprising a semiconductor substrate; a first insulating film formed on the semiconductor substrate; one pair of electrodes; a second insulating film formed in such a manner that the second insulating film covers one pair of the electrodes; and a humidity sensitive film formed on the second insulating film in such a manner that the humidity sensitive film covers one pair of the electrodes and a space between the one-paired electrodes. The one-paired electrodes have been formed on the first insulating in such a manner that these one-paired electrodes are separately located opposite to each other on the same plane. As a result, while the humidity sensitive film whose relative dielectric constant is changed in response to humidity has been interposed between one-pair of the electrodes, the humidity can be detected based upon the change in the relative dielectric constants of the humidity sensitive film.

The conventional capacitance type humidity sensor is arranged by that the detecting unit constituted by the electrodes and the humidity sensitive film is formed on a rigid substrate, e.g., the semiconductor substrate and the glass substrate.

As a consequence, in such a case that the above-explained conventional capacitance type humidity sensor is directly arranged on a mounting unit having a curved plane, since this conventional capacitance type humidity sensor is partially made in contact to the mounting unit, there is a risk that the humidity sensor is broken when external force is applied to this sensor. For instance, the conventional capacitance type humidity sensor is arranged on a windshield of a vehicle in order to be applied to an automatic control operation of an automatic air conditioning system as one of purposes capable of preventing a fogging phenomenon of the windshield of the vehicle.

Also, such a sensor arrangement may be conceived. That is, the conventional capacitance type humidity sensor is arranged on the mounting unit via a buffering member which owns a curved plane formed in correspondence with the curved plane of the mounting unit. In this sensor arrangement, the build of the sensor containing the buffering member becomes large. As a consequence, in particular, when the humidity sensor is mounted on the windshield, this humidity sensor may disturb viewing fields of passengers of the vehicle, resulting in unfavorable results.

Under such a circumstance, the conventional capacitance type humidity sensor has been arranged on a flat unit (for example, on dash panel) which is separated from the mounting unit having the curved plane. As a consequence, errors with respect to a portion which is actually wanted to be measured may be more or less produced.

Conventionally, there are main two different types of humidity sensors, a resistance type humidity sensor and a capacitance type humidity sensor. In view of these conventional humidity sensors, the inventors have preliminary studied a capacitance type humidity sensor as a prototype having a structure shown in FIG. 16.

FIG. 16 indicates a sectional structure of this capacitance type sensor. As indicated in this drawing, an insulating film J2 is formed on a front surface of a semiconductor substrate J1, and also, a plurality of electrodes J4 which are divided by a plurality of trenches J3 are formed on the front surface thereof. The internal portions of the plural trenches J3 are filled with humidity sensitive materials J6 via insulating films J5 which are formed on the front surfaces of these plural electrodes J4.

In the humidity sensor having the above-described structure, since a dielectric constant "∈" of each humidity sensitive member J6 is varied in response to humidity within an atmosphere, capacitances which are formed among these plural electrodes J4 are changed. As a result, this humidity sensor may detect humidity based upon a variation of electric signals in response to the capacitance change. This is disclosed in, for example, Japanese Laid-open Patent Application No. 2002-243689, which corresponds to U.S. Pat. No. 6,445,565-B1.

In the humidity sensor having the above-described structure, electric signals are outputted which respond to the capacitances formed among the plural electrodes J4, so that these electric signal outputs become analog outputs. Therefore, the analog outputs of the humidity sensor must be converted into digital outputs. To this end, an A/D converter is required. As a result, there is such a problem that the circuit arrangement of the humidity sensor becomes complex, and thus, the humidity sensor cannot be made compact.

It should be understood that although the description has been made of the humidity sensor as an example, a similar problem may occur in sensor apparatus for instance, infrared sensors, pressure sensors, which employ the above-explained operating mode.

SUMMARY OF THE INVENTION

In view of the above-described problem, it is an object of the present invention to provide a capacitance type humidity sensor capable of preventing lowering of a response characteristic, and also to provide a method of manufacturing the above-described capacitance type humidity sensor.

Further, it is another object of the present invention to provide a screen printing method capable of printing in higher positioning precision.

Further, it is further another object of the present invention to provide sensor equipment capable of producing a digital sensor output, while an A/D converter is not required.

A capacitance type humidity sensor includes: a detection substrate including a detection portion disposed on a first side of the detection substrate; and a circuit board including a circuit portion. The detection portion detects humidity on the basis of capacitance change of the detection portion. The circuit portion processes the capacitance change of the detection portion as an electric signal. The detection portion is connected to the circuit portion electrically. The detection substrate further includes a sensor pad disposed on a second side of the detection substrate, which is opposite to the first side of the detection substrate. The sensor pad works as a connection terminal for the circuit portion. The sensor pad is electrically connected to the detection portion through a conductor in a through hole of the detection substrate.

In the above sensor, the detection portion and the circuit portion are formed on different boards so that the detection portion has no protection film such as gel. Thus, the response of the humidity is improved.

Preferably, the sensor further includes a sealing member. The circuit board further includes a first pad as a connection terminal for the sensor pad. The first pad is disposed on a first side of the circuit board. The first pad is electrically connected to the circuit portion. The detection substrate and the circuit board are stacked in such a manner that the second side of the detection substrate contacts the first side of the circuit board. The sensor pad is electrically connected to the first pad through a connection member. The sealing member has a ring shape and disposed between the first side of the circuit board and the second side of the detection substrate so that the sealing member seals the sensor pad and the first pad. In this case, the connection portion between the electrode and the circuit portion, i.e., the sensor pad, the first pad and the connection member, are prevented from being eroded. Further, the dimensions of the sensor are reduced.

Preferably, the detection portion includes a pair of comb-teeth electrodes and a humidity sensitive film. The detection substrate is made of a semiconductor substrate. The comb-teeth electrodes are interleaved each other so that the comb-teeth electrodes are separated by a predetermined distance. The humidity sensitive film covers the comb-teeth electrodes and a space between the comb-teeth electrodes. In this case, the facing area of the comb-teeth electrode becomes larger. Thus, the capacitance change between the electrodes becomes larger. Further, the substrate can be made of a glass substrate or a semiconductor substrate. By using the semiconductor substrate, the sensor can be manufactured by a conventional semiconductor process. Thus, the manufacturing cost of the sensor is reduced.

Preferably, the humidity sensitive film is capable of changing relative permittivity of the humidity sensitive film in accordance with the humidity in atmosphere. The circuit board has flexibility so that the circuit board is deformable in accordance with a curvature of a mounting portion. The sensor is mounted on the mounting portion in such a manner that a second side of the circuit board contacts the mounting portion. The second side of the circuit board is opposite to a first side of the circuit board, the first side facing the detection substrate. More preferably, the circuit portion processes the capacitance change between the comb-teeth electrodes as an electric signal.

Further, a method for manufacturing a capacitance type humidity sensor is provided. The method include the steps of: preparing a detection substrate including a detection portion disposed on a first side of the detection substrate; preparing a circuit board including a circuit portion; and electrically connecting between the detection portion and the circuit portion. The detection portion is capable of changing capacitance of the detection portion in accordance with humidity in atmosphere. The circuit portion processes capacitance change of the detection portion as an electric signal. The step of preparing the detection substrate includes a step of forming a sensor pad on a second side of the detection substrate. The second side of the detection substrate is opposite to the first side of the detection substrate. The sensor pad works as a connection terminal for the circuit portion. The sensor pad is electrically connected to the detection portion through a conductor in a through hole of the detection substrate.

In the sensor manufactured by the above method, the detection portion and the circuit portion are formed on different boards so that the detection portion has no protection film such as gel. Thus, the response of the humidity is improved.

Preferably, the step of preparing the circuit board includes a step of forming a first pad on the circuit board as a connection terminal for the sensor pad. The first pad is disposed on a first side of the circuit board. The first pad is electrically connected to the circuit portion. The step of electrically connecting includes steps of: stacking the detection substrate and the circuit board in such a manner that the second side of the detection substrate contacts the first side of the circuit board; electrically connecting between the sensor pad and the first pad through a connection member; and sealing with a sealing member between the first side of the circuit board and the second side of the detection substrate so that the sealing member seals a connection portion between the sensor pad and the first pad. The sealing member has a ring shape.

Further, a method of screen-printing paste on a substrate through a pattern hole of a screen mask by applying the screen mask on the substrate is provided. The method includes the steps of: preparing a standard pattern hole in the screen mask as a positioning standard between the screen mask and the substrate; forming a positioning pattern on the substrate; printing the paste on a dummy substrate by applying the screen mask on the dummy substrate so that a standard pattern is printed on the dummy substrate through the standard pattern hole; detecting a position of the standard pattern on the dummy substrate; positioning the substrate in such a manner that a position of the positioning pattern on the substrate coincides with the position of the standard pattern, which is detected in the step of detecting; and printing the paste on the substrate by applying the screen mask on the substrate in a state where the substrate is positioned in the step of positioning. The positioning pattern has almost the same shape as the standard pattern. The positioning pattern on the substrate is formed in accordance with a positioning relationship between the standard pattern hole and the pattern hole. In this case, the substrate and the screen mask are able to position with high accuracy.

Preferably, the positioning pattern includes a plurality of positioning pattern parts, which are separated each other by a predetermined distance. More preferably, the positioning pattern parts on the substrate sandwich a region on the substrate. In the step of printing the paste, the paste is printed in the region of the substrate through the pattern hole.

Preferably, the substrate includes a pair of electrodes, which are interleaved each other. The paste includes polymer material of a humidity sensitive film. The pattern hole is formed in the screen mask in such a manner that the pattern hole corresponds to a humidity-sensitive-film-to-be-formed region on the substrate. The humidity-sensitive-film-to-be-formed region covers the electrodes and a space between the electrodes. More preferably, the positioning pattern on the substrate is provided by a portion not to be covered with the humidity sensitive film.

Further, sensor equipment for generating an output in accordance with a physical quantity as a detection object includes: a decoder; and a semiconductor substrate including a plurality of memory cells, each of which includes a transistor for switching and a capacitor. The transistor in each memory cell includes a source region, a drain region, and a gate electrode. The source region and the drain region have a first conductive type. The gate electrode is disposed on the semiconductor substrate through a gate insulation film in such a manner that the gate electrode is sandwiched between the source region and the drain region. The capacitor in each memory cell includes a trench, a semiconductor region, a dielectric film, and a capacitance electrode. The trench is disposed in the semiconductor substrate. The semiconductor region having the first conductive type is disposed in the trench, and connected to the source region.

The dielectric film is capable of changing dielectric constant of the dielectric film in accordance with the physical quantity. The dielectric film is embedded in the semiconductor region in the trench in such a manner that the dielectric film is disposed on a surface of the semiconductor region. The capacitance electrode is disposed on a surface of the dielectric film through an insulation film in such a manner that the capacitance electrode faces the trench. The trench in each memory cell has an opening area, which is different in each memory cell. The decoder detects a state of each memory cell whether the memory cell is in a written state or in an unwritten state, and outputs the output in accordance with the state of the memory.

In the above equipment, since the opening area of each trench is different, the physical quantity written in each memory cell is different. Thus, the physical quantity can be obtained as a digital value. Thus, the sensor equipment is capable of producing a digital sensor output without an A/D converter.

Preferably, the trench in each memory cell has a width, which is different in each memory cell so that the opening area of the trench is different in each memory cell. More preferably, the width of the trench in each memory cell is obtained by multiplying a predetermined width by two to the Nth power, and N represents natural number.

Further, sensor equipment for generating an output in accordance with a physical quantity as a detection object includes: a decoder; and a semiconductor substrate including a plurality of memory cells, each of which includes a transistor for switching and a capacitor. The transistor includes a source region, a drain region, and a gate electrode. The source region and the drain region have a first conductive type. The gate electrode is disposed on the semiconductor substrate through a gate insulation film in such a manner that the gate electrode is sandwiched between the source region and the drain region. The capacitor includes a pair of comb-teeth electrodes and a dielectric film. The comb-teeth electrodes are disposed on the semiconductor substrate. The dielectric film is capable of changing dielectric constant of the dielectric film in accordance with the physical quantity. The dielectric film fills a space between the comb-teeth electrodes. The comb-teeth electrodes are separated each other by a distance. The distance of a pair of the comb-teeth electrodes in each memory cell is different in each memory cell. The decoder detects a state of each memory cell whether the memory cell is in a written state or in a unwritten state, and outputs the output in accordance with the state of the memory.

In the above equipment, since the distance between the electrodes in each memory cell is different, the physical quantity written in each memory cell is different. Thus, the physical quantity can be obtained as a digital value. Thus, the sensor equipment is capable of producing a digital sensor output without an A/D converter.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS (First Embodiment)

Figure 1A:
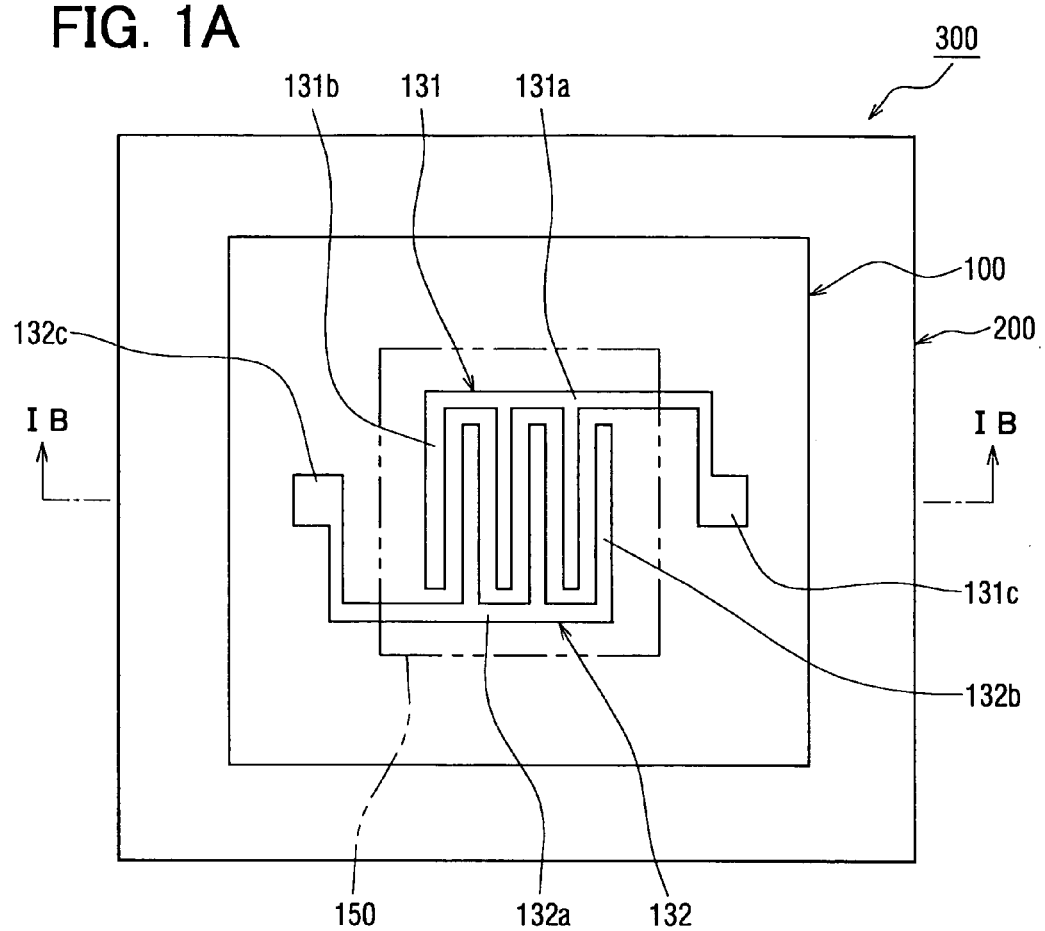
FIG. 1A is a plan view showing a capacitance type humidity sensor according to a first embodiment of the present invention.
Figure 1B:
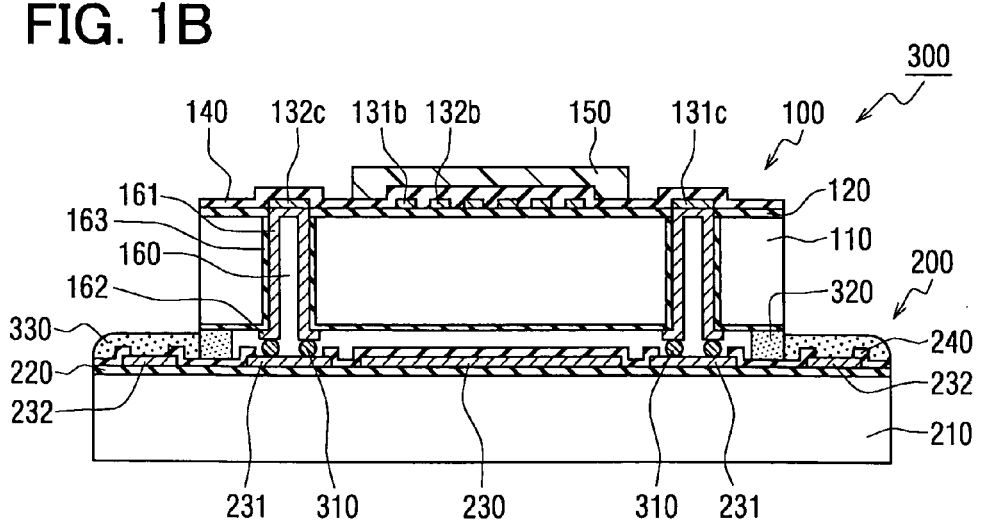
FIG. 1B is a cross sectional view showing the sensor taken along line IB—IB in FIG. 1A.

FIGS. 1A and 1B are a diagram for schematically showing a structure of a capacitance type humidity sensor 300 according to a first embodiment mode; FIG. 1A is a plan view for representing this capacitance type humidity sensor 300; and FIG. 1B is a sectional view for showing the humidity sensor, taken along a line IB—IB of FIG. 1A. It should be noted that for the sake of convenience, in FIG. 1A, one pair of electrodes located under both a humidity sensitive film and a second insulating film are illustrated in a transmission manner.

As indicated in FIG. 1A and FIG. 1B, the capacitance type humidity sensor 300 has been constituted by a detection board 100 and a circuit board 200. A detecting unit whose capacitance is changed in response to humidity has been provided on the side of one plane of the detection board 100. A circuit unit for processing a capacitance change of the detecting unit has been provided on the circuit board 200.

First, a description is made of the detection board 100. Reference numeral 110 shows a semiconductor material functioning as a substrate, and the semiconductor substrate 110 has been made of silicon in this first embodiment mode. Then, one pair of electrodes 131 and 132 has been formed via a silicon oxide film 120 functioning as an insulating film. The electrodes 131 and 132 have been arranged in such a manner that these electrodes 131 and 132 are separated from each other and are positioned opposite to each other on the same plane over the silicon oxide film 120.

Although the shapes of the electrodes 131 and 132 are specifically not limited, in this first embodiment mode, as shown in FIG. 1A, the respective electrodes 131 and 132 have been constituted by common electrode portions 131*a* and 132*a*, and a plurality of comb-teeth-shaped electrode portions 131*b* and 132*b* (in FIG. 1, three electrode portions). These plural comb-teeth-shaped electrode portions 131*b* and 132*b* are extended from the common electrode portions 131*a* and 132*a* along one direction, respectively. Then, one pair of electrodes 131 and 132 has been arranged in such a manner that the comb-teeth-shaped electrodes 131*b* and 132*b* of one pair of the electrodes 131 and 132 are alternately arrayed with each other. As previously explained, since the comb-teeth-shaped shapes are employed as the shapes of one pair of the electrodes 131 and 132, while the arranging areas of the electrodes 131 and 132 can be made small, such areas that these comb-teeth-shaped electrode portions 131*b* and 132*b* are positioned to each other can be made large. As a result, a change amount of an electrostatic capacitance between the electrodes 131 and 132 is increased which is changed in response to a humidity change in a peripheral portion thereof, so that the sensitivity of the capacitance type humidity sensor 300 can be improved.

As the electrodes 131 and 132, wiring materials, for instance, Al, Ag, Au, Cu, Ti, Poly-Si, and the like may be applied. However, since noble metals (such as Au) having an anti-corrosion characteristic with respect to water contents are high cost and constitute a contamination source in a semiconductor process, these electrodes 131 and 132 may be manufactured by employing aluminum in this first embodiment mode, while aluminum electrodes are low cost and can be manufactured in a semiconductor process.

As a consequence, in this first embodiment mode, a silicon nitride film 140 has been formed as a protection film on the semiconductor substrate 110 in such a manner that this silicon nitride film 140 covers these one-paired electrodes 131 and 132. As a result, the corrosion of these electrodes 131 and 132 caused by the water contents may be suppressed.

A humidity sensitive film 150 made of a polymer material having a hydroscopic property has been formed on the silicon nitride film 140 in such a manner that this humidity sensitive film 150 covers one pair of these electrodes 131 and 132, and the space between these electrodes 131 and 132. As the polymer material, polyimide, butyric acid/acetic acid cellulose, and the like may be applied. In this first embodiment mode, the humidity sensitive film 150 has been formed by employing polyimide. The one-paired electrodes 131 and 132, and the humidity sensitive film 150 constitute the detecting unit. It should be understood that in FIG. 1A, a rectangular area which is surrounded by a broken line indicates an area where the humidity sensitive film 150 is formed.

Also, as shown in FIG. 1A, electrode pads 131*c* and 132*c* have been formed on edge portions of the electrodes 131 and 132. Then, a through hole 160 has been formed in both a semiconductor substrate 110 and a silicon oxide film 120 while the electrode pads 131*c* and 132*c* are used as bottom portions. The electrode pads 131*c* and 132*c* have been formed via a conductor 161 arranged inside the through hole 160 on rear planes of the semiconductor substrate 110 where the electrodes 131 and 132 are formed. The electrode pads 131*c* and 132*c* have been electrically connected to a sensor pad 162 which functions as a connection terminal for connecting the circuit unit of the circuit board 200. This sensor pad 162 has been exposed in order to be connected to the circuit unit of the circuit board 200. As the structural material of the conductor 161, if this conductor 161 can be arranged within the through hole 160, then there is no specific limitation. In this first embodiment mode, this conductor 161 has been formed by employing Al in a similar manner to those of the electrodes 131 and 132 in this first embodiment mode. It should also be noted that reference numeral 163 indicates an insulating layer.

Next, a description is made of the circuit board 200. In FIG. 1B, reference numeral 210 shows a semiconductor material functioning as a substrate. In this first embodiment mode, the semiconductor substrate 210 has been manufactured by silicon. Then, a circuit unit 230 has been formed on the front plane of the semiconductor substrate 210. This circuit unit 230 (contains, for example, a C-V converting circuit for converting capacitance into voltage), and processes a change in capacitances defined between the electrodes 131 and 132 so as to obtain an electric signal. This circuit unit 230 has been constructed of, for instance, CMOS transistors and the like. In this first embodiment mode, for the sake of convenience, only such a wiring portion within the circuit unit 230 has been represented, while this wiring portion has been made of Al, and has been formed on the semiconductor substrate 210 via a silicon oxide film 220 functioning as an insulating film.

Also, a first pad 231 has been formed as a connection terminal on the silicon oxide film 220. The first pad 231 has been electrically connected via a wiring unit (not shown) to the circuit unit 230 and this connection terminal is used so as to be connected to the sensor pad 162 of the detection board 100. Also, a second pad 232 has been formed as an external connection terminal in such an area which is not overlapped with the detection board 100 on the outer peripheral side from the first pad 231 under stacked layer condition (will be discussed later) in order to derive the signal processed in the circuit unit 230 to an external unit. This external connection terminal has been electrically connected via a wiring unit (not shown) to the circuit unit 230. It should also be noted that in this first embodiment mode, both the first pad 231 and the second pad 232 have been formed by employing Al in a similar to the electrodes 131 and 132.

Also, reference numeral 240 represents a silicon nitride film which functions as a protection film capable of preventing corrosion of the circuit unit 230. Both the first pad 231 and the second pad 232 have been exposed with respect to the silicon nitride film 240.

Both the detection board 100 and the circuit board 200 which have been manufactured in the above-explained structures have been stacked in such a manner that the sensor pad forming plane of the detection board 100 are located opposite to the first pad forming plane of the circuit board 200. Under this stacked condition, the sensor pad 162 of the detection board 100 has been connected via a connecting material 310 (for example, solder) to the first pad 231 of the circuit board 200. In other words, since the sensor pad 162 is connected to the first pad 231 on the rear plane side of the forming plane where the electrodes 131 and 132 are formed, these electrodes 131 and 132 have been electrically connected to the circuit unit 230.

Also, a sealing member 320 has been arranged between the sensor pad forming plane of the detection board 100 and the first pad forming plane of the circuit board 200 in a ring shape. As a result, both a connection portion between the sensor pad 162 and the first pad 231, and the circuit unit 230 have been sealed in a hermetical manner. As the sealing material 320, under such a condition that a material has been arranged between the sensor pad forming plane of the detecting board 100 and the first pad forming plane of the circuit board 200, if this material can hermetically seal both the connection portion between the sensor pad 162 and the first pad 231 and the circuit unit 230 in combination with both the sensor pad forming plane and the first pad forming plane, then any sealing material may be employed. In this first embodiment mode, an epoxy-series adhesive agent has been applied as the sealing material 320 so as to seal the connection portion and the circuit unit 230 in the hermetical manner, and also to fix the detection board 100 to the circuit board 200. As a consequence, reliability as to connections between the sensor pad 162 (electrodes 131 and 132) and the first pad 231 (circuit unit 230) can be improved.

Furthermore, the second pad 232 formed on the outer peripheral side from the arranging position of the sealing member 320 has been protected by a protecting member 330. This protecting member 330 is employed so as to prevent corrosion of the second pad 232. In this first embodiment mode, silicon gel has been applied as this protecting member 330. It should also be noted that although the second pad 232 has been connected via a bonding wire, or the like to the external unit, for the sake of convenience, it is omitted in this first embodiment mode.

In the capacitance type humidity sensor 300 with employment of the above-described structure, when water contents osmose into the humidity sensitive film 150, since the water contents own a large relative dielectric constant, a relative dielectric constant of the humidity sensitive film 150 is changed in response to the amount of the osmosed water contents. As a result, an electrostatic capacitance of a capacitor is changed which is constituted by one pair of these electrodes 131 and 132 while the humidity sensitive film 150 is used as a portion of a dielectric substance, and then, this capacitance change is processed by the circuit unit 230 so as to be converted into a voltage. The amount of the water contents contained in the humidity sensitive film 150 may correspond to the humidity around the capacitance type humidity sensor 300, so that humidity can be detected based upon the electrostatic capacitance between one-pair of these electrodes 131 and 132.

Figure 2A:
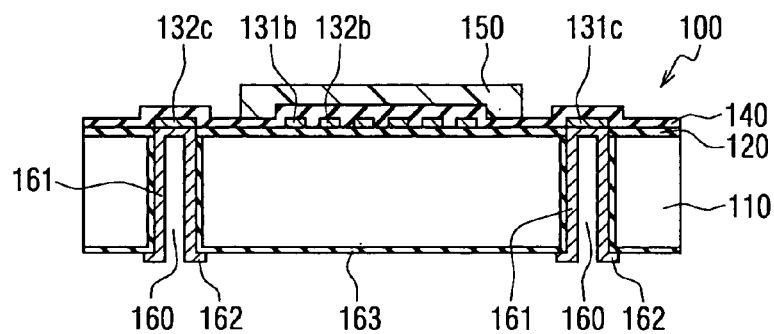
FIG. 2A is a cross sectional view explaining a detection substrate preparing process in a method for manufacturing the sensor.
Figure 2B:
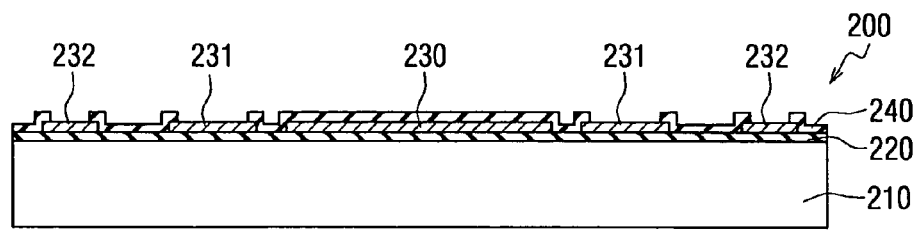
FIG. 2B is a cross sectional view explaining a circuit board preparing process in the method.
Figure 2C:
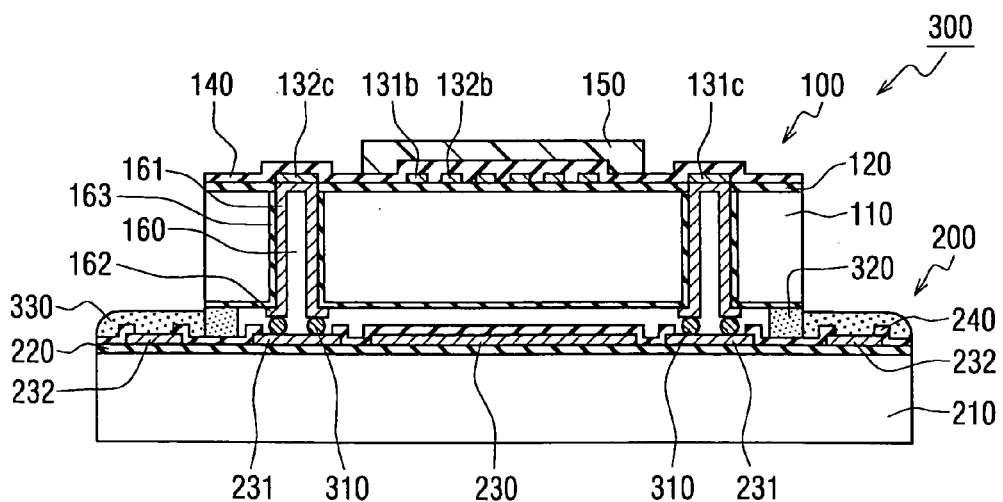
FIG. 2C is a cross sectional view explaining a connection process in the method, according to the first embodiment.

Next, a method for manufacturing the capacitance type humidity sensor 300 with employment of the above-described structure will now be explained with reference to FIG. 2A to FIG. 2C. FIG. 2 is a sectional view for indicating an example of manufacturing steps for the manufacturing method of the capacitance type humidity sensor 300; FIG. 2A indicates a detection board preparing step; FIG. 2B shows a circuit board preparing step; and FIG. 2C represents a connection step.

First, the detection board preparing step is carried out. That is, as shown in FIG. 2A, the silicon oxide film 120 corresponding to an insulating film is formed on the front surface of the semiconductor substrate 110 by way of, for example, a CVD (Chemical Vapor Deposition) method, and aluminum (i.e., Al) is deposited on the silicon oxide film 120 by employing, for instance, a vapor deposition method, and then, the deposited aluminum is patterned so as to form the electrodes 131 and 132. After the electrodes 131 and 132 have been formed, the silicon nitride film 140 corresponding to a protection film is manufactured byway of, for instance, a plasma CVD method in such a manner that this silicon nitride film 140 covers the upper portions of the electrodes 131 and 132, and also, covers the space between the electrodes 131 and 132. Then, the humidity sensitive film 150 is formed in a predetermined area on the silicon nitride film 140 in such a manner that this silicon nitride film 140 covers the upper portions of the electrodes 131 and 132, and also, covers the space between the electrodes 131 and 132.

In this case, as the method for forming the humidity sensitive film 150, a spin coat method and a screen printing method may be applied. In this first embodiment mode, the screen printing method was carried out by employing paste which was made of the precursor of polyimide (namely, precursor of humidity sensitive film in which polyamide acid is employed as basic skeleton) so as to deposit this paste on the silicon oxide film 140 corresponding to the uppermost front surface of the semiconductor substrate 11. Thereafter, this deposited paste was heated at a predetermined temperature and hardened (to form imide), so that the humidity sensitive film 150 made of polyimide was formed.

Furthermore, the sensor pad 162 which constitutes the connection terminal with respect to the circuit board 200 is formed on the rear surface of the electrode forming plane of the semiconductor substrate 110. A mask (not shown) is formed on the rear surface of the semiconductor substrate 110, and then, the semiconductor substrate 110 is etched by using such an etching fluid as, for example, a TMAH solution (tetramethyleammonium hydroxide solution). After the etching process, the silicon oxide film 120 on the etched area of the semiconductor substrate 110 is removed, and the through hole 160 is formed while the sensor pad 162 is used as the bottom portion.

Then, after the insulating layer 163 has been formed on both the rear surface of the electrode forming plane of the semiconductor substrate 110 and the side plane of the through hole 160, for instance, aluminum is vapor-deposited from the rear surface side of the semiconductor substrate 110, and the deposited aluminum is patterned. As a result, the conductor 161 is formed within the through hole 160, and also, the sensor pad 162 connected to this conductor 161 is formed on the rear surface of the electrode forming plane of the semiconductor substrate 110. It should be noted that as to the methods for forming the through hole 160, the conductor 161, and the sensor pad 162, the present invention is not limited only to the above-described example. For instance, when the conductor 161 is formed, a screen printing method and an inkjet printing method may be alternatively applied. It is preferable to provide a large number of metals within the through hole 160.

Next, the circuit board preparing step is carried out. That is, a portion of the circuit unit 230 is formed on the surface of the semiconductor substrate 210 by way of, for example, an ion implantation method, a thermal diffusion method, a CVD method, or the like. Subsequently, the silicon oxide film 220 corresponding to the insulating film is formed by way of, for example, a CVD method, and a contact hole (not shown) is formed, and thereafter, aluminum (Al) is deposited on the silicon oxide film 220 by employing, for instance, a vapor deposition method. Then, since the deposited aluminum is patterned, the circuit unit 230, the first pad 231, and the second pad 232 are formed, and further, a wiring portion (not shown) is formed which connects the circuit unit 230, the first pad 231, and the second pad 232 to each other.

Furthermore, in this first embodiment mode, the silicon nitride film 240 corresponding to the protection film is formed on these structural elements by way of, for example, a plasma CVD method. In this case, in order that the circuit board 200 is electrically connected to the detection board 100 and the external unit, the silicon nitride film 240 formed on both the first pad 231 and the second pad 232 is removed by way of an etching process. It should also be noted that as to the manufacturing timing of the detection board preparing step and the circuit board preparing step, any one of these preparing steps may be firstly carried out, or may be alternatively carried out in a parallel manner.

Then, under such a condition that both the detection board 100 and the circuit board 200 are prepared, the connection step is carried out. That is, while a connecting material (namely, soldering material in this first embodiment mode) is coated on the first pad 231 of the circuit board 200, under such a condition that the detection board 100 is positioned in such a manner that the sensor pad 162 is located opposite to the first pad 231, for instance, a heating tool (not shown) abuts against the electrode forming plane of the detection board 100. Then, the heating tool heats this electrode forming plane, while the heating tool applies pressure to the electrode forming plane along the direction of the circuit board 200. As a result, the connecting material 310 is melted, so that the sensor pad 162 is joined to the first pad 231, and thus, the electrodes 131 and 132 are electrically connected to the circuit unit 230.

After the sensor pad 162 has been connected to the first pad 231, the epoxy-series adhesive agent functioning as the sealing member 320 is injected in the ring shape into a gap formed between the sensor pad forming plane of the detection board 100 and the first pad forming plane of the circuit board 200, and then, this epoxy-series adhesive agent is heated so as to be hardened. As a result, both the connection portion between the sensor pad 162 and the first pad 231, and also, the circuit unit 230 are sealed in the hermetical manner by the sensor pad forming plane of the detection board 100, the first pad forming plane of the circuit board 200, and the sealing material 320. Thus, the capacitance type humidity sensor 300 is manufactured in accordance with the above-described manufacturing manner.

It should also be noted that since the second pad 232 corresponds to the external connection terminal which is used so as to derive the signals processed by the circuit unit 230 to the external unit, this second pad 232 (and connection portion thereof) is covered/protected by the protecting material 330 such as silicon gel in order to prevent the corrosion thereof after, for example, a characteristic investigation of the capacitance type humidity sensor 300 has been accomplished, or after the second pad 232 has been connected via a bonding wire (not shown) to the external unit. It should also be noted that although the second pad 232 has been connected via a bonding wire, or the like to the external unit, for the sake of convenience, it is omitted also in this first embodiment mode.

As previously explained, in accordance with the structure of the capacitance type humidity sensor 300 of this first embodiment mode, the detecting unit constructed of the electrodes 31, 32, and the humidity sensitive film 50, and the circuit unit 230 have been provided on the different boards 100 and 200. The sensor pad 162 functioning as the connection terminal with the circuit unit 230 has been provided on the rear surface of the detecting unit forming plane in the detection board 100. As a result, since the protecting material such as gel need not be provided on the detecting unit which is different from that of the conventional capacitance type humidity sensor, lowering of the response characteristic of this humidity sensor 300 can be avoided.

Also, in this first embodiment mode, under such a condition that the detection board 100 and the circuit board 200 have been stacked in such a manner that the sensor pad forming plane of the detection board 100 is located opposite to the first pad forming plane of the circuit board 200, the sensor pad 162 has been connected via the connecting material 310 to the first pad 231. Also, this connection portion has been hermetically sealed with respect to the outer atmosphere by the sensor pad forming plane, the first pad forming plane, and the sealing member 320. As a result, it is possible to prevent the corrosion of the connection portion between the sensor pad 162 and the first pad 231, and further, the build of the sensor 300 along the plane direction can be made compact. In other words, if the dimension of this sensor 300 is equal to the dimension of the conventional sensor along the plane direction, then the area of the detecting unit of this sensor 300 can be made larger than that of the conventional sensor, so that the sensitivity of this sensor 300 can be improved.

Also, while both the circuit unit 230 and the first pad 231 have been formed on the same plane side of the semiconductor substrate 210, the circuit unit 230 has been hermetically sealed with respect to the outer atmosphere by the sensor pad forming plane, the first pad forming plane, and the sealing member 320 in combination with the first pad 231. As a consequence, even when the silicon nitride film 240 functioning as the protection film is not provided on the circuit unit 230 (silicon oxide film 210), the corrosion of the circuit unit 230 can be prevented. It should also be understood that in this first embodiment mode, the silicon nitride film 240 has been formed in the step after the circuit board 200 has been formed up to the connection step in order to avoid that the circuit unit 230 is adversely influenced by the outer atmosphere.

Also, the second pad 232 has been formed on the first pad forming plane of the circuit board 200 on the outer peripheral side from the arranging position of the sealing member 320. This second pad 232 is employed so as to derive the signals processed in the circuit unit 230 to the external unit. As a consequence, even under such a condition that the connection portion between the sensor pad 162 and the first pad 231 has been previously sealed by the sealing member 320 in the hermetical manner, for instance, a tester abuts against the second pad 232 so as to perform the characteristic test, and alternatively, the sensor 300 may be electrically connected via the second pad 232 to the external unit. Also, since the second pad 232 has been provided on the plane which is different from the electrode forming plane, the second pad 232 can be covered/protected by the protecting material 330 while the electrodes 131 and 132 and the humidity sensitive film 150 are not covered.

While the preferred embodiment modes of the present invention have been described, the present invention is not limited only to the above-explained embodiment modes, but may be modified in various modes.

This first embodiment mode has exemplified such an example that the semiconductor substrate 110 made of silicon has been employed as the board which constitutes the detection board 100, and both the electrodes 131 and 132 have been formed on this semiconductor substrate 110 via the silicon oxide film 120. As previously explained, if the semiconductor substrate 110 is employed as the substrate, then the detection board 100 can be formed by way of a general-purpose semiconductor process, so that the manufacturing cost can be reduced. However, as the substrate, an insulating substrate such as a glass substrate may be applied.

Similarly, the first embodiment mode has exemplified such an example that the semiconductor substrate 210 has been employed as the board which constitutes the circuit board 200, and the circuit board 200 has been formed by utilizing a semiconductor process. However, the circuit board 200 is not limited only to the above-described example, but, ceramics and a resin may be applied as the board.

Figure 3:
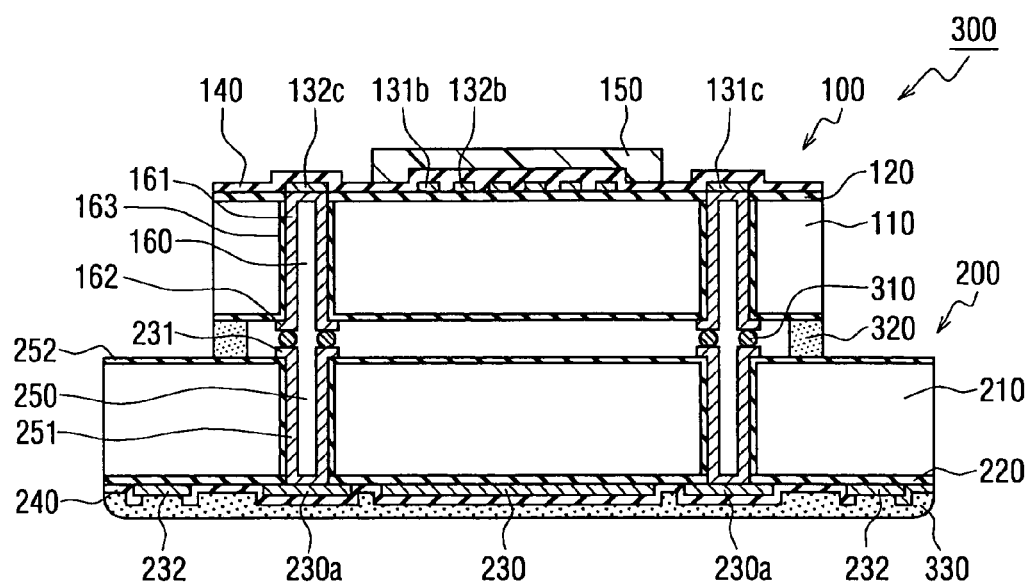
FIG. 3 is a cross sectional view showing a capacitance type humidity sensor according to a modification of the first embodiment.

Also, this first embodiment mode has exemplified such an example that the circuit unit 230 has also been hermetically sealed by the sensor pad forming plane of the detection board 100, the first pad forming plane of the circuit board 200, and the sealing member 320. In other words, such an example has been exemplified in which both the circuit unit 230 and the first pad 231 have been formed on the same plane side of the semiconductor substrate 210. However, as shown in FIG. 3, the sensor 300 may be alternatively constructed in such a manner that the circuit unit 230 is provided on the rear surface side of the first pad forming plane. That is, FIG. 3 is a sectional view for schematically showing a modification of this first embodiment mode, namely corresponds to FIG. 1B.

In the case of such an alternative structure, the circuit unit 230 may be covered by the protecting material 330 such as silicon gel. It should be understood that in FIG. 3, reference numeral 250 indicates a through hole formed in the semiconductor substrate 210, reference numeral 251 shows a conductor within the through hole 250, reference numeral 252 denotes an insulating layer, and also, the circuit unit 230 has been connected to the conductor 251 by an edge pad 230a of the circuit unit 230. Also, while the second pad 232 has been provided on the forming plane side of the circuit unit 230, this second pad 232 has been covered/protected by the protecting material 330. However, since the protecting material 330 is not provided on the rear plane side of the first pad forming plane in the sensor structure shown in FIG. 1A and FIG. 1B, the build of the sensor 300 along the stacking layer direction can be made compact.

It should also be understood that the structure where the detection board 100 and the circuit board 200 are stacked is not limited only to the above-described structure. Alternatively, another structure may be employed in which, for example, only the second pad 232 is formed on the rear plane side of the first pad forming plane.

Also, in order to electrically connect the electrodes 131 and 132 to the circuit unit 230, the present invention is not limited only to such a structure that the detection board 100 and the circuit board 200 are stacked with each other. For instance, the sensor pad 161 and the first pad 231 which are provided on the rear plane of the electrode forming plane may be connected to each other by employing a bonding wire. If such a structure is employed in which at least a connection terminal used to be connected to the external unit is not provided on the electrode forming plane side of the detection board 100, then the protecting material 33 is not arranged on the detecting unit constituted by the electrodes 131 and 132, and the humidity sensitive film 150. As a result, lowering of the response characteristic can be prevented.

Also, this first embodiment mode has exemplified such an example that one pair of the electrodes 131 and 132 have been formed in the comb-teeth shape manner. However, if such a structure is made by interposing the humidity sensitive film 150 between one pair of these electrodes 131 and 132, then no specific restriction is made in the structure of the detecting unit.

(Second Embodiment)

It should be understood that in the below-mentioned embodiment modes, a screen printing method according to the present invention is applied to forming of a humidity sensitive film of a capacitance type humidity sensor 400 which is manufactured by interposing a humidity sensitive film between one pair of electrodes, while a relative dielectric constant of the humidity sensitive film is changed in response to humidity.

Figure 4A:
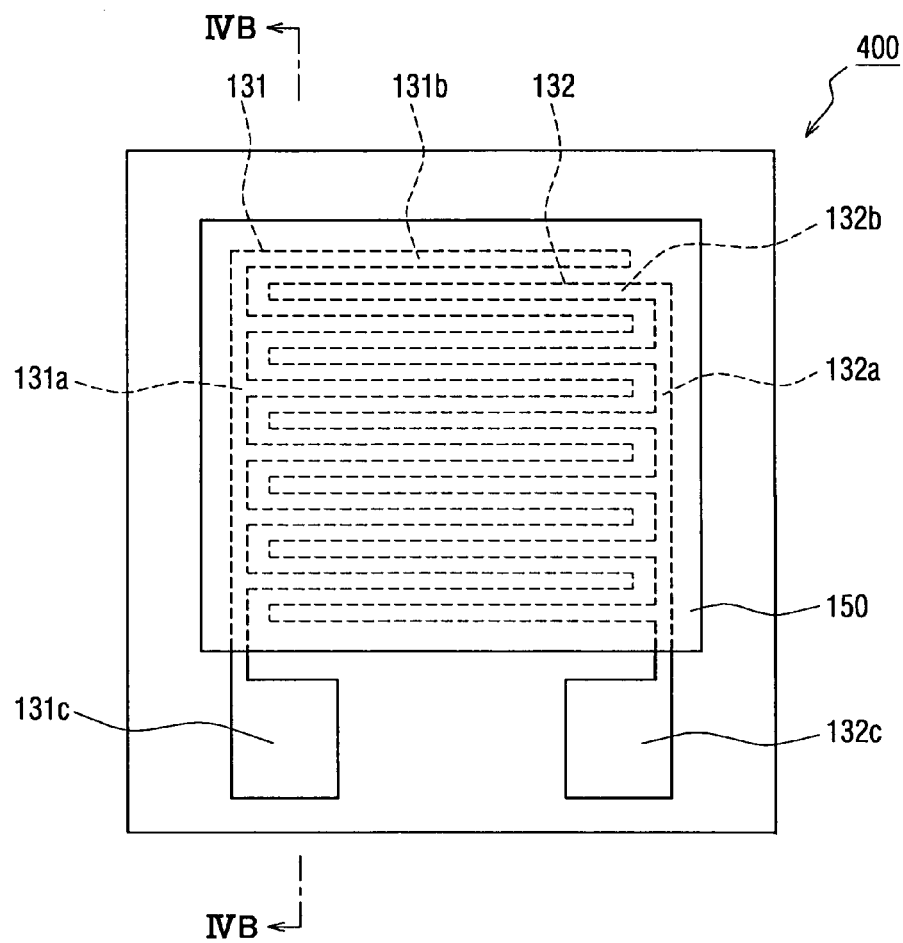
FIG. 4A is a plan view showing a capacitance type humidity sensor according to a second embodiment of the present invention.
Figure 4B:
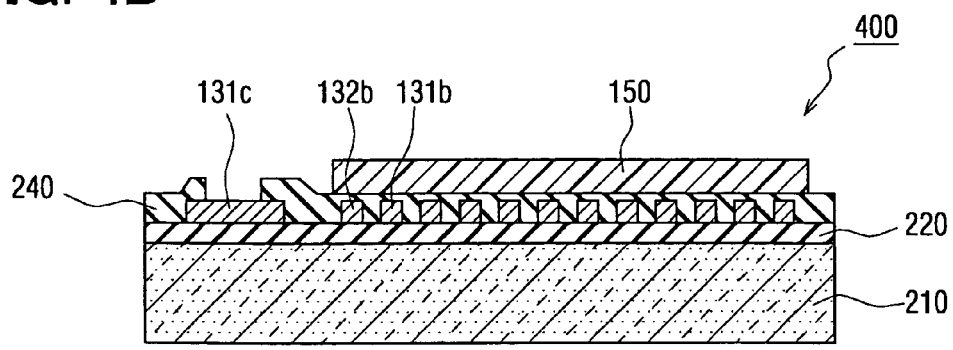
FIG. 4B is a cross sectional view showing the sensor taken along line IVB—IVB in FIG. 4A.

A first description is made of a schematic structure of a capacitance type humidity sensor 400 with reference to FIGS. 4A snd 4B. FIG. 4A is a plan view for representing this capacitance type humidity sensor 400, and FIG. 4B is a sectional view for showing the humidity sensor 400, taken along a line IVB—IVB of FIG. 4A. It should be noted that for the sake of convenience, in FIG. 4A, one pair of electrodes located under both a humidity sensitive film and a second insulating film are illustrated in a transmission manner. Also, in FIG. 4A and FIG. 4B, only a peripheral portion of a detecting unit is illustrated. In the detecting unit, a capacitance is changed in response to a humidity change of the peripheral portion thereof.

In FIG. 4A, reference numeral 210 shows a semiconductor substrate functioning as a substrate, and the semiconductor substrate 210 has been made of silicon in this embodiment mode. Then, a silicon oxide film 220 functioning as a first insulting film has been formed on an upper plane of the semiconductor substrate 210. One pair of electrodes 131 and 132 have been arranged in such a manner that these electrodes 131 and 132 are separated from each other and are positioned opposite to each other on the same plane over the silicon oxide film 220.

Although the shapes of the electrodes 131 and 132 are specifically not limited, in this embodiment mode, as shown in FIG. 4A, the respective electrodes 131 and 132 have been constituted by common electrode portions 131a and 132a, and a plurality of comb-teeth-shaped electrode portions 131b and 132b. These plural comb-teeth-shaped electrode portions 131b and 132b are extended from the common electrode portions 131a and 132a along one direction, respectively. Then, one pair of electrodes 131 and 132 have been arranged in such a manner that the comb-teeth-shaped electrodes 131b and 132b of one pair of the electrodes 131 and 132 are alternately arrayed with each other. As previously explained, since the comb-teeth-shaped shapes are employed as the shapes of one pair of the electrodes 131 and 132, while the arranging areas of the electrodes 131 and 132 can be made small, such areas that these comb-teeth-shaped electrode portions 131b and 132b are positioned to each other can be made large. As a result, a change amount of an electrostatic capacitance between the electrodes 131 and 132 is increased which is changed in response to a humidity change in a peripheral portion thereof, so that the sensitivity of the capacitance type humidity sensor 400 can be improved.

As the electrodes 131 and 132, wiring materials, for instance, Al, Ag, Au, Cu, Ti, Poly-Si, and the like may be applied. In this first embodiment mode, these electrodes 131 and 132 have been manufactured by employing aluminum (Al). It should be noted that the comb-teeth-shaped portions 131b and 132b correspond to electrodes defined in a scope of claims for patent, and the common electrode portions 131a and 132a correspond to wiring portions defined in the scope of claims for patent.

Also, in this embodiment mode, a silicon nitride film 240 has been formed as a second insulating film on the semiconductor substrate 210 in such a manner that this silicon nitride film 240 covers these one-paired electrodes 131 and 132. As a result, the corrosion of these electrodes 131 and 132 caused by the water contents may be suppressed. In such a case that the electrodes 131 and 132 owns, for example, an anticorrosion characteristic with respect to water contents, the humidity sensor 400 may be arranged without the silicon nitride film 240.

As indicated in FIG. 4A, it should be noted that while pads 131c and 132c functioning as external connection terminals have been formed at edge portions of these electrodes 131 and 132, these electrodes 131 and 132 have been electrically connected via these pads 131c and 132c to a correcting circuit for correcting an output, and a signal processing circuit for detecting a change amount of electrostatic capacitances. These pads 131c and 132c must be exposed so as to be connected to the correcting circuit and the like, and thus, these pads 131c and 132c are not covered by the silicon nitride film 240. Also, in this embodiment mode, since the semiconductor substrate 210 has been employed as the substrate for constituting the capacitance type humidity sensor 400, the above-explained correcting circuit and the like may be formed on the same substrate.

A humidity sensitive film 150 made of a polymer material having a hydroscopic property has been formed on the silicon nitride film 240 in such a manner that this humidity sensitive film 150 covers one pair of these electrodes 131 and 132, and the space between these electrodes 131 and 132. As the polymer material, polyimide, butyric acid/acetic acid cellulose, and the like may be applied. In this embodiment mode, the humidity sensitive film 150 has been formed by employing polyimide. It should also be noted that as the forming method, such a screen printing method capable of eliminating a patterning operation by a photo-process is applied. The manufacturing method will be explained later.

In the capacitance type humidity sensor 400 with employment of the above-described structure, when water contents osmose into the humidity sensitive film 150, since the water contents own a large relative dielectric constant, a relative dielectric constant of the humidity sensitive film 150 is changed in response to the amount of the osmosed water contents. As a result, an electrostatic capacitance of a capacitor is changed which is constituted by one pair of these electrodes 131 and 132 while the humidity sensitive film 150 is used as a portion of a dielectric substance. The amount of the water contents contained in the humidity sensitive film 150 may correspond to the humidity around the capacitance type humidity sensor 400, so that humidity can be detected based upon the electrostatic capacitance between one-pair of these electrodes 131 and 132.

Figure 5A:
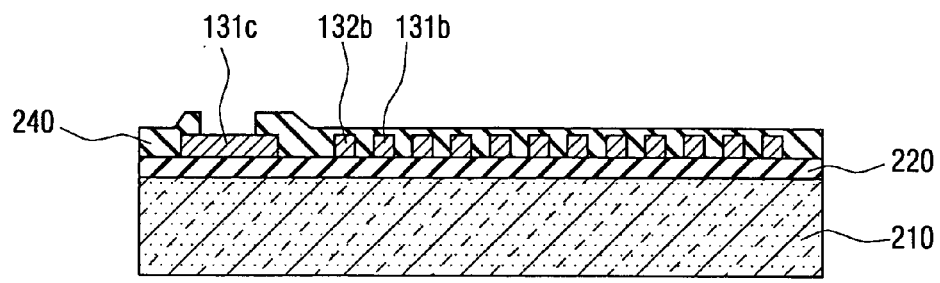
FIG. 5A is a cross sectional view explaining an electrode forming process in a method for manufacturing the sensor.
Figure 5B:
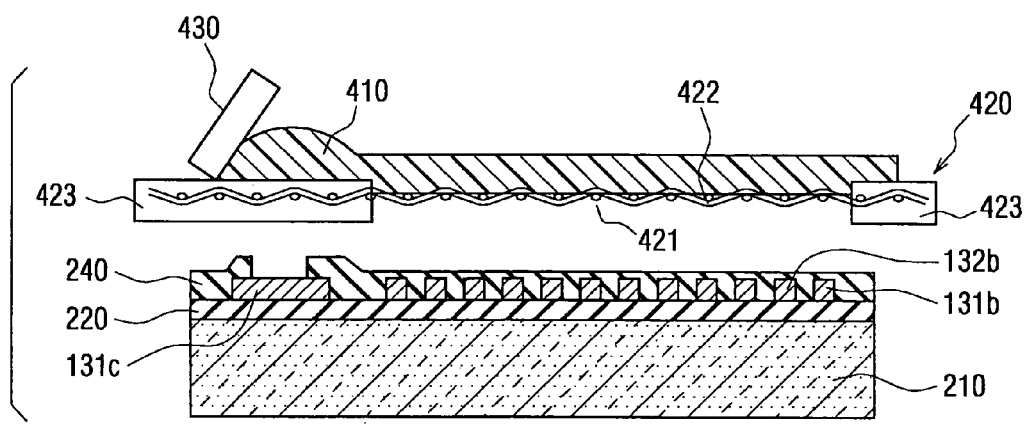
FIG. 5B is a cross sectional view explaining a printing process in the method.
Figure 5C:
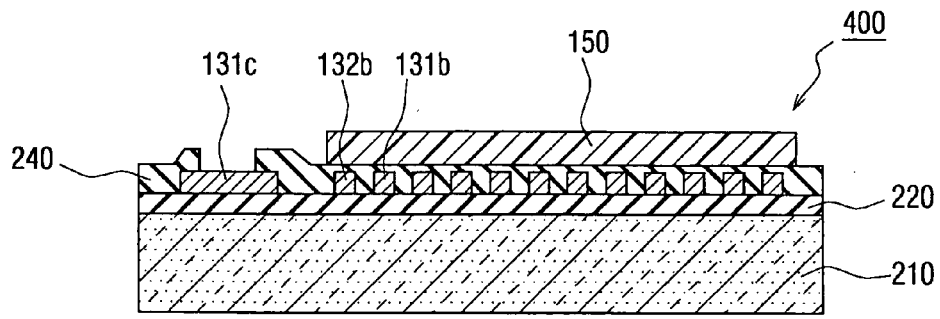
FIG. 5C is a cross sectional view explaining a humidity sensitive film forming process in the method, according to the second embodiment.

Next, a method for manufacturing the capacitance type humidity sensor 400 will now be explained with reference to FIG. 5A to FIG. 5C. FIGS. 5A to 5C are sectional view for indicating manufacturing steps for the manufacturing method of the capacitance type humidity sensor 400 according to this embodiment mode; FIG. 5A indicates an electrode forming step; FIG. 5B shows a printing step; and FIG. 5C represents a step after a humidity sensitive film has been formed. It should be understood that although the semiconductor substrate 210 is normally provided under wafer state, for the sake of convenience, only a portion thereof is illustrated.

As shown in FIG. 5A, first of all, the electrode forming step is carried out. The silicon oxide film 220 corresponding to a first insulating film is formed on the front surface of the semiconductor substrate 210 by way of, for example, a CVD (Chemical Vapor Deposition) method, and then, the electrodes 131 and 132 (comb-teeth-shaped electrode portions 131b, 132b, and pad 131c are indicated in this drawing) are formed by way of, for example, a vapor deposition method by employing Al. In this embodiment mode, in this step, the silicon nitride film 240 corresponding to a second insulating film is further manufactured by way of, for instance, a plasma CVD method in such a manner that this silicon nitride film 240 covers the upper portions of the electrodes 131 and 132, and also, covers the space between the electrodes 131 and 132.

Next, as shown in FIG. 5B, the printing step used to form the humidity sensitive film 150 is carried. In this printing step, the semiconductor substrate 210 after the electrodes 131 and 132 have been formed is transported to a screen printing apparatus, and then, the screen printing apparatus performs a screen printing operation by employing paste 410 which contains a polymer material corresponding to the structural material of the humidity sensitive film 150.

Concretely speaking, a screen mask 420 is prepared in order that pattern holes 421 corresponding to a forming area of the humidity sensitive film 150 have been provided, while this screen mask 420 is made by coating emulsion 423 on a mesh screen 422 (for instance, stainless steel screen having 250 meshes). Then, this screen mask 420 abuts against a front surface (forming plane side of electrodes 131 and 132) of the semiconductor substrate 210. Thereafter, paste 410 made of a precuror (namely, precuror humidity sensitive film in which polyamide acid is used as basic skeleton) of polyimide is supplied onto this screen mask 420. Since a squeeze 130 is slid, the paste 410 is printed via the pattern hole 421 on the silicon nitride film 240 corresponding to the uppermost front surface of the semiconductor substrate 210. Further, after the printing step, when the printed paste 410 is heated at a predetermined temperature and hardened (to form imide), the humidity sensitive film 150 made of polyimide is formed, as indicated in FIG. 5C. Then, the humidity sensitive film 150 is processed in a dicing step (not shown) so as to be cut in the unit of a chip.

On the other hand, in the above-described capacitance type humidity sensor 400, since the sensor build is made compact, the positional precision of the humidity sensitive film 150 is required, and thus, the screen mask 420 must be precisely positioned with respect to the semiconductor substrate 210.

In connection to this requirement, in the conventional screen printing operation, the following method has been carried out. That is, firstly, the screen mask 420 abuts against the dummy substrate (namely, for example, such a semiconductor substrate 210 that electrodes 131, 132, and the like are not formed), and the paste is screen-printed. Then, the position of the printing area which has been printed through the pattern holes 421 is detected by employing the imaging apparatus such as a CCD camera. Then, the semiconductor substrate 210 is positioned on the stage in order that the detected printing area and the humidity sensitive film forming area (area where humidity sensitive film 150 is wanted to be formed) on the semiconductor substrate 210 may become substantially same positions. Under this positioning condition, the printing operation is carried out.

Figure 6:
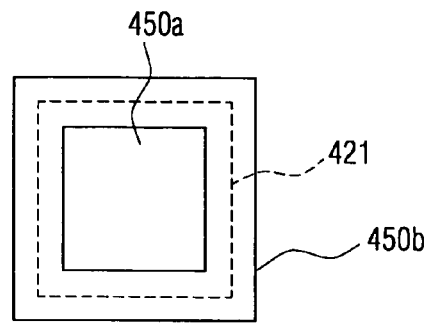
FIG. 6 is a plan view explaining a comparison method for positioning, according to a comparison of the second embodiment.

However, in the case of the screen printing operation, it is practically difficult to uniform the thickness of the paste 410 (namely, humidity sensitive film 150) printed on the front surface of the semiconductor substrate 210. This reason is caused by that, for instance, a so-called "saddle" phenomenon occurs in edge areas. As a consequence, as shown in FIG. 6, since the humidity sensitive film forming area 50a in the semiconductor substrate 210 is made larger than the pattern holes 421 (area surrounded by broken line in FIG. 6) of the screen mask 420, such an effective area that the film thicknesses of the paste 410 may become substantially uniform is arranged in the humidity sensitive film forming area 450a.

Also, in the case of the screen printing operation, since the squeeze 430 is slid so as to print the paste 410, the shapes and/or dimensions of areas which are actually printed are more or less different from those of the pattern holes 421 due to extensions of the mesh screen 422. As a consequence, for example, as shown in FIG. 6, there are such differences in the shapes and/or dimensions between the humidity sensitive film forming area 450a of the semiconductor substrate 210 and the printed area 450b which has been actually printed on the dummy substrate. Thus, even when the positioning operation of the semiconductor substrate 210 is carried out while the printed area 450b is employed as the reference area, the humidity sensitive film 150 cannot be formed in the higher positioning precision. It should also be noted that FIG. 6 is a schematic diagram for explaining the conventional positioning operation. In FIG. 6, for the sake of convenience, the shape of the printed area 450b is made equal to that of the pattern holes 421 (and humidity sensitive film forming area 450a).

Figure 7A:
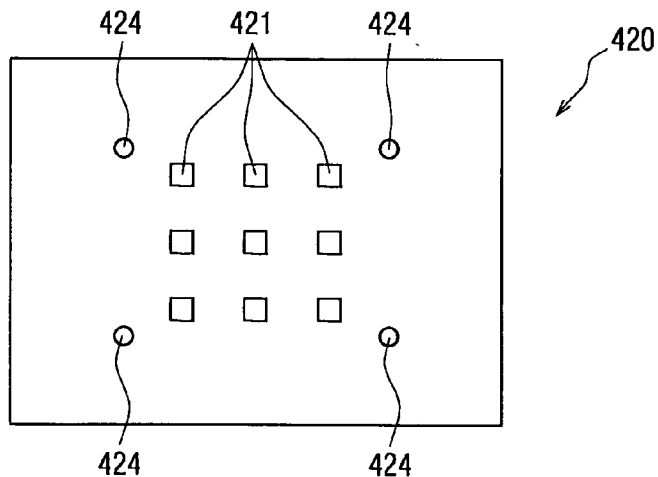
FIGS. 7A to 7C are plan views showing a standard pattern hole and a positioning pattern, according to the second embodiment.
Figure 7B:
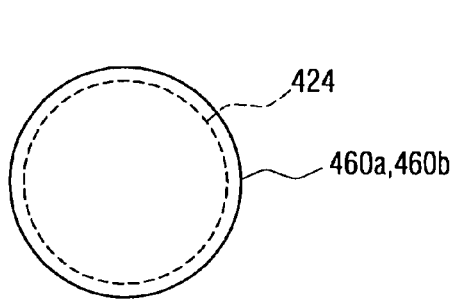
Figure 7C:
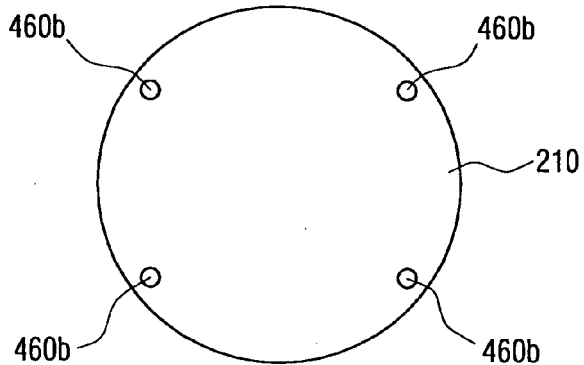
Figure 8A:
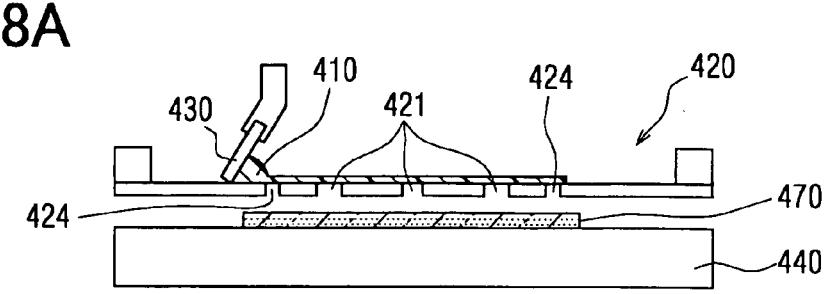
FIG. 8A is a cross sectional view explaining a printing step of printing to a dummy substrate in a printing process.
Figure 8B:
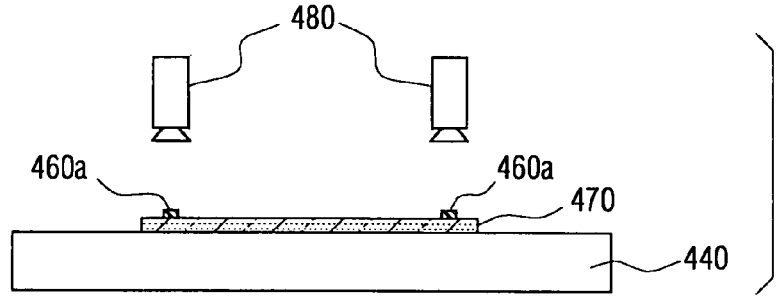
FIG. 8B is a cross sectional view explaining a position detection step of detecting a standard pattern in the printing process.
Figure 8C:
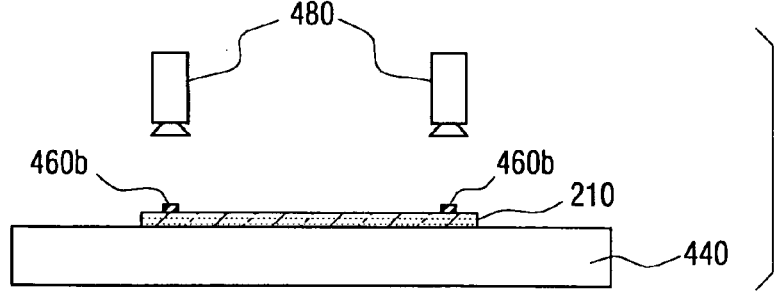
FIG. 8C is a cross sectional view explaining a positioning step of positioning a semiconductor substrate in the printing process.

In this first embodiment mode, the above-described printing step (FIG. 5B) is carried out in accordance with the below-mentioned method. This printing step will now be explained with employment of FIG. 7A to FIG. 7C, and FIG. 8A to FIG. 8D. FIG. 7A to FIG. 7C are diagrams for explaining a reference pattern hole and a positioning pattern. Also, FIG. 8 is a diagram for explaining the printing step shown in FIG. 5B in more detail; FIG. 8A explanatorily shows a printing operation to the dummy substrate; FIG. 8B explanatorily indicates a position detecting operation of the reference pattern; FIG. 8c explanatorily represents a positioning operation of the semiconductor substrate 10; and FIG. 8D explanatorily shows a printing operation to the semiconductor substrate 10.

As indicated in FIG. 7A, in this embodiment mode, reference pattern holes 424 have been formed in the screen mask 420, while the reference pattern holes 424 constitute a positioning reference with respect to both this screen mask 420 and the semiconductor substrate 210. Concretely speaking, a plurality (4 pieces in total) of circular-shaped reference pattern holes 424 have been provided at positions where these reference pattern holes 124 are located opposite to each other by sandwiching the pattern holes 421 which form the humidity sensitive film 150. A diameter of each of these reference pattern holes 424 has been set to a range (for instance, 300 μm) larger than, or equal to 100 μm, and smaller than, or equal to 1,000 μm.

Also, as indicated in FIG. 7B, a positioning pattern 460b having a shape and a dimension which are substantially equal to those of a reference pattern 460a was formed on the semiconductor substrate 210 in response to the positional relationship between the pattern holes 421 and the reference pattern holes 424, as represented in FIG. 7C. The reference pattern 460a has been printed via the reference pattern holes 424 (namely, area surrounded by broken line in FIG. 7B) along the plane direction of the semiconductor substrate 210. Concretely speaking, in a chip which is used to form the capacitance type humidity sensor 400, the positioning pattern 460b has been formed by that the silicon nitride film 240 was deposited on a predetermined area, and the silicon nitride film 240 was also deposited at a predetermined position of a chip area which is different from the chip used to form the capacitance type humidity sensor 400. Alternatively, the positioning pattern 460b may be formed based upon such a shape which has been previously printed on the semiconductor substrate 210 (under such a condition that structural elements up to silicon oxide film 240 have been formed) via the reference pattern holes 424, or may be formed based upon such a shape which has been previously printed on the dummy substrate via the reference pattern holes 424.

Then, under such a condition that both the screen mask 420 having the above-explained structure and the semiconductor substrate 210 (under such a status that silicon nitride film 240 and positioning pattern 460b by this silicon nitride film 240 have been formed) have been prepared, first of all, as shown in FIG. 8A, the dummy substrate 470 (namely, semiconductor substrate 210 where electrodes 131 and 132 are not formed) was provisionally positioned and fixed to the stage 440 of the screen printing apparatus. Thereafter, the stage 440 was fed up to a setting position of the screen mask 420, and while the screen mask 420 abutted against the dummy substrate 470, the paste 410 which becomes the humidity sensitive film 150 was printed. At this time, a printing condition of the dummy substrate 470 was made substantially identical to a printing condition (will be explained later) of the semiconductor substrate 210. In this embodiment mode, the height of the stage 440 was adjusted, and an interval between the lower plane of the screen mask 420 and the front surface of the dummy substrate 470 was made substantially equal to an interval between the lower plane of the screen mask 420 and the front surface of the semiconductor substrate 210. Otherwise, as the dummy substrate 470, such a substrate having the substantially same thickness as that of the semiconductor substrate 210 may be alternatively applied.

Next, under such a condition that the stage 440 was returned from the setting position of the screen mask 420 to a substrate setting position, the reference pattern 460a printed on the dummy substrate 470 was imaged by a CCD camera 480 installed above the substrate setting position so as to detect a position (coordinate value) of the reference pattern 460a with respect to the stage 440. Concretely speaking, the coordinate value of the reference pattern 460a was defined by scalers (two sets of scalers along x direction and y direction) which are displayed on a monitor in a superimposing manner with the image of the reference pattern 460a.

After the position of the reference pattern 460a was defined, the dummy substrate 470 was dismounted from the stage 440, and then, the semiconductor substrate 210 was positioned on the stage 440 so as to be fixed thereon. Concretely speaking, as indicated in FIG. 8C, the positioning pattern 460b was imaged by the CCD camera 480, and then, the position of the semiconductor substrate 210 was adjusted in such a manner that the positioning pattern 460b is made coincident with the positions which have been defined by the scalers.

Figure 8D:
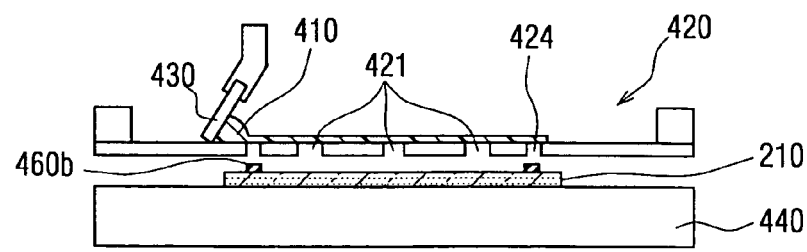
FIG. 8D is a cross sectional view explaining a printing step of printing to the semiconductor substrate, according to the second embodiment.

Then, under this positioning condition, the stage 440 was transported to the setting side of the screen mask 420, and then, as indicated in FIG. 8D, the screen mask 420 abutted against the semiconductor substrate 210, and the paste 410 which constitutes the humidity sensitive film 150 was printed. It should also be noted that FIG. 8D corresponds to the previous drawing of FIG. 5B. Also, in FIG. 8C and FIG. 8D, for the sake of convenience, the electrodes 131 and 132 formed on the semiconductor substrate 210 are omitted, and only the positioning pattern 460b is illustrated.

As previously described, in accordance with the screen printing method of this embodiment mode, since both the positioning pattern 460b formed on the semiconductor substrate 210 and the reference pattern 460a printed on the dummy substrate 470 have the substantially same shapes and the substantially same dimensions, the semiconductor substrate 210 and the screen mask 420 can be positioned in higher positioning precision. As a consequence, the printing operation by way of the pattern holes 421 for forming the humidity sensitive film 150 can be carried out in higher positioning precision with respect to the humidity sensitive film forming area 450a on the semiconductor substrate 210.

It should be noted that the positioning pattern 460b corresponds to such a portion which may constitute the positioning reference between the screen mask 420 and the semiconductor substrate 210 instead of the humidity sensitive film forming area 450a in which the paste 410 is wanted to be printed via the pattern holes 421 on the semiconductor substrate 210. Since the shape and/or the dimension of this positioning pattern 460b are not fixed due to its characteristic which is different from the humidity sensitive film forming area 450a, this positioning pattern 460b can be manufactured in such a manner that the shape and/or the dimension of this positioning pattern 460b are made nearly equal to those of the reference pattern 460a printed via the reference pattern holes 424.

Also, in this embodiment mode, such an example was exemplified. That is, a plurality of positioning patterns 460b were provided at the opposing positions by sandwiching the humidity film forming area 450a. As a consequence, even when the differences in both the shapes and the dimensions between the reference pattern hole 424 and the printed reference pattern 460a are different from each other depending upon the forming positions of the positioning patterns 460b, the printing operation by the pattern holes 421 can be carried out in the higher positioning precision.

Also, in such a case that the humidity sensitive film 150 is made of polyimide as represented in this embodiment mode, since the emulsion 423 which constitutes the screen mask 420 is required to have a chemical resistance characteristic, the resist thickness by the emulsion 423 must be made thick. As a consequence, if the dimension of the reference pattern hole 424 is smaller than 100 µm, then the printed reference pattern 460a cannot be formed as a fine pattern. However, in this embodiment mode, since the dimension (diameter) of the reference pattern hole 424 along the plane direction of the semiconductor substrate 210 is set within the range larger than, or equal to 100 µm and smaller than, or equal to 1,000 µm, the reference pattern 460a printed on the dummy substrate 470 can be made as the fine pattern, so that the reference pattern 460a can be readily positioned.

While the preferred embodiment modes of the present invention have been described, the present invention is not limited only to the above-explained embodiment modes, but may be modified in various modes.

This embodiment mode has exemplified such an example that the semiconductor substrate 210 made of silicon has been employed as the substrate, and both the electrodes 131 and 132 have been formed on this semiconductor substrate 210 via the insulating film 220. As previously explained, if the semiconductor substrate 210 is employed as the substrate, then the capacitance type humidity sensor 400 can be formed by way of a general-purpose semiconductor process, so that the manufacturing cost can be reduced. However, as the substrate, an insulating substrate such as a glass substrate may be applied. Also, the screen printing method of the present invention is not limited only to the formation of the humidity sensitive film 150 of the capacitance type humidity sensor 400, but may be applied to such a method that, for example, conductive paste is printed on a printed board.

Figure 9A:
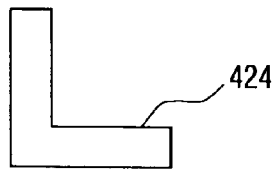
FIGS. 9A and 9B are plan views showing standard pattern holes according to modifications of the second embodiment.
Figure 9B:
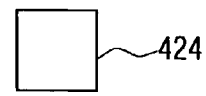

Also, in this embodiment mode, such an example has been indicated that the shapes of the reference pattern holes 424 are circular. When the reference pattern holes 424 are made circular, there is a small shape difference between the reference pattern holes 424 and the reference pattern 460a which has been printed via these reference pattern holes 424, and further, clogging can be hardly conducted because of no corner portion, and the position of the reference pattern 460a printed on the dummy substrate 470 can be readily defined (detected). However, since the positioning pattern 460b is also made substantially circular, there is a risk that the semiconductor substrate 210 is shifted along the rotation direction with respect to the screen mask 120 while the positioning pattern 460b is located at a center in a single reference pattern hole 124 and the positioning pattern 460b. To the contrary, for instance, as indicated in FIG. 9A, if the shapes of the reference pattern holes 124 and the shape of the positioning pattern 60b are made in substantially L-shapes, the position (namely, two directions along plane direction) of the semiconductor substrate 210 may be readily determined with respect to the stage 440 even when one piece of the reference pattern hole 424 is employed. It should also be noted that the shapes of the reference pattern holes 424 are not limited only to the above-explained example, but may be alternatively polygonal shapes (as one example, rectangle shown in FIG. 9B). In particular, if a plurality of these reference pattern shapes 424 are employed, then the semiconductor substrate 210 may be positioned in higher positioning precision.

Also, this embodiment mode has exemplified such an example that the positioning pattern 460b has been provided in the area which is different from the forming area of the capacitance type humidity sensor 400 of the semiconductor substrate 210. However, such a portion which is not covered by the humidity sensitive film 150 may be alternatively applied as the positioning pattern 460b within the capacitance type humidity sensor 400. For example, the pads 131c and 132c may be alternatively employed so as to function as the positioning pattern 460b. In this alternative case, since the positioning pattern 460b need not be separately formed, the sensor build can be made compact, and the manufacturing cost thereof can be lowered.

Also, this embodiment mode has exemplified such an example that the dimension of the reference pattern holes 424 formed in the screen mask 420 has been set within the range larger than, or equal to 100 µm and smaller than or equal to 1,000 µm. However, in this embodiment mode, the paste 410 forms polyimide functioning as the humidity sensitive film 150, and the resist thickness of the emulsion 423 is made thick due to the chemical resistance characteristic, the dimension of the reference pattern hole 424 is selected to be larger than, or equal to 100 µm. As a result, since the resist thickness may be made thin, depending upon the sort of the paste 410, the dimension of the reference pattern holes 424 formed in the screen mask 120 along the plane direction of the semiconductor substrate 10 may be alternatively set within the range larger than, or equal to 50 µm and smaller than, or equal to 1,000 µm. In the case of the dimension smaller than 50 µm, the reference pattern 460a printed from the mesh size which constitutes the screen mask 420 can be hardly made as fine patterns. It should also be noted that since the chip size where the capacitance type humidity sensor 400 is formed is normally selected from approximately 1,000 µm to 2,000 µm, the maximum dimension thereof is selected to be smaller than, or equal to 1,000 µm. Also, as to the minimum dimension, in the case of a circle, the minimum dimension is set as the diameter thereof. In the case of the L-shape shown in FIG. 9, and of the polygonal shape, the minimum dimension is set as one edge.

(Third Embodiment)

Figure 10A:
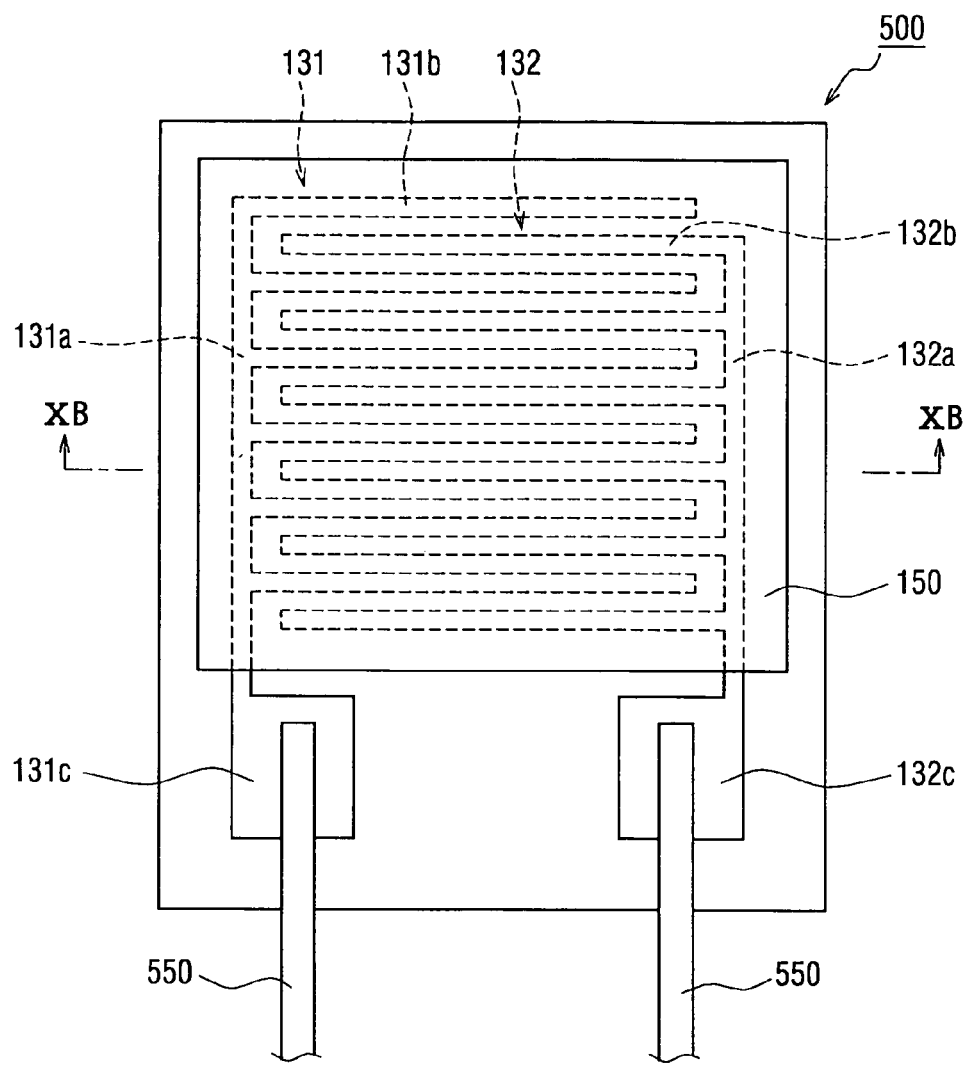
FIG. 10A is a plan view showing a capacitance type humidity sensor according to a third embodiment of the present invention.
Figure 10B:
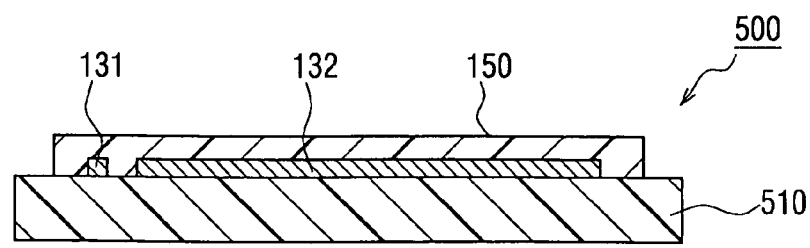
FIG. 10B is a cross sectional view showing the sensor taken along line XB—XB in FIG. 10A.

FIGS. 10A and 10B are a diagram for schematically showing a structure of a capacitance type humidity sensor 500 according to a third embodiment mode; FIG. 10A is a plan view for representing this capacitance type humidity sensor 500; and FIG. 10B is a sectional view for showing the humidity sensor 500, taken along a line XB—XB of FIG. 10A. It should be noted that for the sake of convenience, in FIG. 10A, one pair of electrodes located under a humidity sensitive film are illustrated by a broken line.

In FIG. 10A and FIG. 10B, reference numeral 510 shows a substrate, to which a flexible substrate having flexibility has been applied in this embodiment mode. If materials own flexibility as a structural material of the substrate 510, then there is no specific limitation. Thus, in this embodiment mode, a thermoplasitic resin film made of a liquid crystal polymer (LCP) having a thickness of 25 µm has been applied to the structural material of the substrate 510.

Then, one pair of electrodes 131 and 132 have been arranged in such a manner that these electrodes 131 and 132 are separated from each other and are positioned opposite to each other on the same plane over the substrate 510. Although the shapes of the electrodes 131 and 132 are specifically not limited, in this embodiment mode, as shown in FIG. 10A, the respective electrodes 131 and 132 have been constituted by common electrode portions 131a and 132a, and a plurality of comb-teeth-shaped electrode portions 131b and 132b. These plural comb-teeth-shaped electrode portions 131b and 132b are extended from the common electrode portions 131a and 132a along one direction, respectively. Then, one pair of electrodes 131 and 132 have been arranged in such a manner that the comb-teeth-shaped electrodes 131b and 132b of one pair of the electrodes 131 and 132 are alternately arrayed with each other. As previously explained, since the comb-teeth-shaped shapes are employed as the shapes of one pair of the electrodes 131 and 132, while the arranging areas of the electrodes 131 and 132 can be made small, such areas that these comb-teeth-shaped electrode portions 131b and 132b are positioned to each other can be made large. As a result, a change amount of an electrostatic capacitance between the electrodes 131 and 132 is increased which is changed in response to a humidity change in a peripheral portion thereof, so that the sensitivity of the capacitance type humidity sensor 500 can be improved.

The electrodes 131 and 132 may be formed by that, for instance, a conductive foil adhered to a single plane of the substrate 510 is etched so as to obtain a desirable pattern. As the conductive foil, a metal foil having a low resistance such as Au, Ag, Cu, and Al may be employed. In this embodiment mode, an Au foil has been employed. It should also be noted that the formation of these electrodes 131 and 132 may be carried out by employing, for example, a printing method other than the etching method of the conductive foil.

It should be noted that in such a case that the electrodes 131 and 132 own no anticorrosion characteristic with respect to water contents, since a protection film is formed on the substrate 510 in such a way that this protection film covers one pair of electrodes 131 and 132, the corrosion of these electrodes 131 and 132 caused by the water contents may be suppressed.

Also, as indicated in FIG. 10A, the electrodes 131 and 132 own pad portions 131c and 132c functioning as external connection terminals at edge portions thereof. These electrodes 131 and 132 have been electrically connected via a lead 550 which is connected to the pad portions 131c and 132c by employing solder, or the like, to a circuit unit (circuit board) on which a signal processing circuit has been formed, while this signal processing circuit may correct an output signal and may detect a change amount of an electrostatic capacitance. These pad portions 131c and 132c must be exposed so as to be connected to the lead 550, and thus, these pad portions 131c and 132c are not covered by a humidity sensitive film (will be explained later).

A humidity sensitive film 150 made of a polymer material having a hydroscopic property has been further formed on the substrate 510 in such a manner that this humidity sensitive film 150 covers one pair of these electrodes 131 and 132, and the space between these electrodes 131 and 132. As the polymer material, polyimide, butyric acid/acetic acid cellulose, and the like may be applied. In this embodiment mode, the humidity sensitive film 150 has been formed by employing polyimide. It should also be noted that as the forming method, although various methods may be conceived, such a screen printing method capable of eliminating a patterning operation by a photo-process has been applied in this embodiment mode.

In the capacitance type humidity sensor 500 with employment of the above-described structure, when water contents osmose into the humidity sensitive film 150, since the water contents own a large relative dielectric constant, a relative dielectric constant of the humidity sensitive film 150 is changed in response to the amount of the osmosed water contents. As a result, an electrostatic capacitance of a capacitor is changed which is constituted by one pair of these electrodes 131 and 132 while the humidity sensitive film 150 is used as a portion of a dielectric substance. The amount of the water contents contained in the humidity sensitive film 150 may correspond to the humidity around the capacitance type humidity sensor 500, so that humidity can be detected based upon the electrostatic capacitance between one-pair of these electrodes 131 and 132.

Figure 11A:
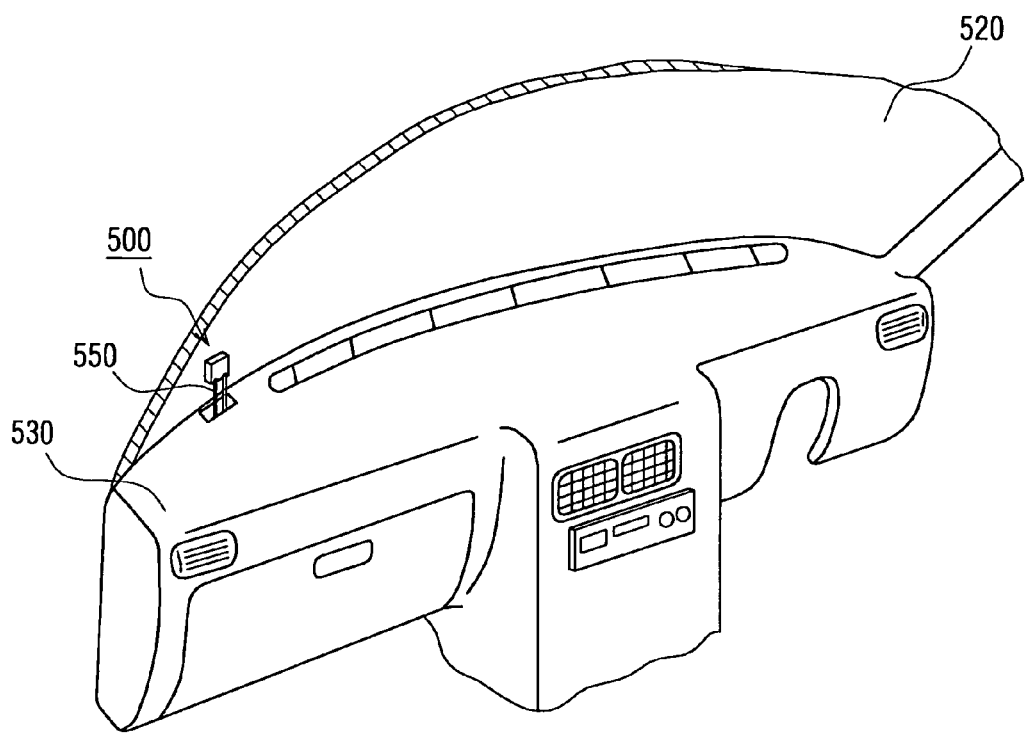
FIG. 11A is a schematic perspective view showing a mounting state of the sensor mounted on a windshield of a vehicle.
Figure 11B:
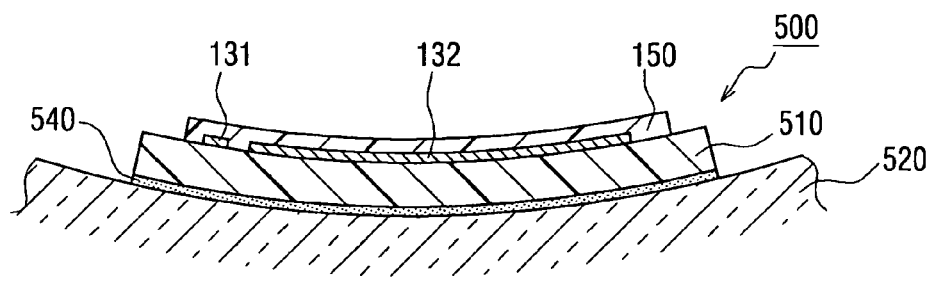
FIG. 11B is a partially enlarged cross sectional view showing the sensor in FIG. 11A, according to the third embodiment.

Next, a featured portion of the capacitance type humidity sensor 500 indicated in this embodiment mode will now be explained by employing FIG. 11A and FIG. 11B. FIG. 11 is a diagram for explanatorily showing such a mounting example that the capacitance type humidity sensor 500 shown in this embodiment mode is mounted on a curved plane of a mounting unit; FIG. 11A is a structural diagram for showing such a case that the capacitance type humidity sensor 500 has been mounted on a windshield functioning as the mounting unit; and FIG. 11B is an enlarged sectional view for representing a peripheral portion of the sensor 500 in FIG. 11A.

In order to apply the capacitance type humidity sensor 500 to an automatic control operation of a automatic air conditioning system as one of purposes capable of preventing a fogging phenomenon of a windshield of a vehicle, it is desirable to detect humidity in the vicinity of the windshield in high precision. However, in such a case that the conventional capacitance humidity sensor using the rigid substrate is directly arranged with respect to a curved plane of the windshield (namely, windshield 520 in FIG. 11A), since this conventional capacitance type humidity sensor is partially made in contact to the mounting unit, there is a risk that the conventional capacitance type humidity sensor is broken when external force is applied to this sensor.

Also, such a sensor arrangement may be conceived. That is, the conventional capacitance type humidity sensor is arranged on the mounting unit via the buffering member which owns the curved plane formed in correspondence with the curved plane of the windshield. In this sensor arrangement, the build of the capacitance type humidity sensor containing the buffering member becomes large. In other words, since a range for disturbing a viewing field of passengers (in particular, vehicle driver in case that sensor is mounted on windshield 520) is increased, an unfavorable result is obtained.

Under such a circumstance, the conventional capacitance type humidity sensor has been arranged on a flat unit (for example, on dash panel 530) which is separated from the windshield having the curved plane. As a consequence, errors with respect to a portion which is actually wanted to be measured may be more or less produced.

To the contrary, in the capacitance type humidity sensor 500 according to this embodiment mode, while the substrate 510 has the flexibility, as indicated in FIG. 11A and FIG. 11B, when this capacitance type humidity sensor 500 is arranged in such a manner that a rear surface of an electrode forming plane of the substrate 510 is located opposite to an inner plane of the windshield 520, this humidity sensor 500 can be deformed in correspondence with the curved plane of the windshield 520. As previously explained, the capacitance type humidity sensor 500 according to this first embodiment mode can be directly arranged even on a mounting unit having a curved plane such as the windshield 520. In other words, the capacitance type humidity sensor 500 can detect humidity in higher precision. It should also be noted that in FIG. 11A, the other end of the lead 550 whose one end has been connected to the capacitance type humidity sensor 500 has been electrically connected to a circuit unit (not shown) positioned under the dash panel 530. Also, in FIG. 11B, reference numeral 540 indicates an adhesive layer, and a double-face tape has been employed as this adhesive layer in this embodiment mode.

Also, the capacitance type humidity sensor 500 has been fixed on the inner plane of the windshield 520 under such a condition that this humidity sensor 500 is deformed in correspondence with the curved plane of the windshield 520. As a consequence, even when external force is applied to the capacitance type humidity sensor 500, since stress is distributed, this capacitance type humidity sensor 500 of the embodiment mode can have a stronger structure with respect to the external force rather than the structure in which the conventional capacitance type humidity sensor 500 is directly arranged on the windshield 520.

Also, the capacitance type humidity sensor 500 according to this embodiment mode can be deformed in correspondence with not only such a curved plane having a predetermined "R", but also another curved plane having an arbitrary "R." As a result, for example, although "R" shapes of curved planes as to the windshield 520 are different from each other depending upon sorts of vehicles, the same capacitance type humidity sensor 500 may be properly applied. As apparent from the foregoing descriptions, this capacitance type humidity sensor 500 may be arranged not only on a curved plane, but also on a flat plane. Furthermore, the capacitance type humidity sensor 500 may be arranged on, for instance, a corner portion of a prism, or the like.

Also, in this embodiment mode, while the circuit unit and the detecting unit constituted by both the electrodes 131 and 132 and the humidity sensitive film 150 have been separately provided, these circuit unit and detecting unit have been electrically connected via the lead 550 to each other. When such an arrangement is employed, the build of the capacitance type humidity sensor 500 arranged on the windshield 520 can be made compact. In other words, disturbances of the viewing fields of the passengers can be reduced. However, the humidity sensor 500 may be alternatively arranged in such a manner that the circuit unit is provided on such a substrate 510 where both the electrodes 131 and 132, and the humidity sensitive film 150 have been provided. In this alternative case, since the electrodes 131 and 132 may be formed, and at the same time, the wiring line which constitutes the circuit unit may be formed, the manufacturing steps may be simplified.

While the preferred embodiment modes of the present invention have been described, the present invention is not limited only to the above-explained embodiment modes, but may be modified in various modes.

This embodiment mode has exemplified such an example that the capacitance type sensor 500 has been arranged on the front surface of the windshield 520 of the vehicle as the mounting unit. However, the capacitance type humidity sensor 500 indicated in this embodiment mode may be alternatively arranged with respect to a mounting unit having another curved plane other than the above-explained example.

(Fourth Embodiment)

Figure 12:
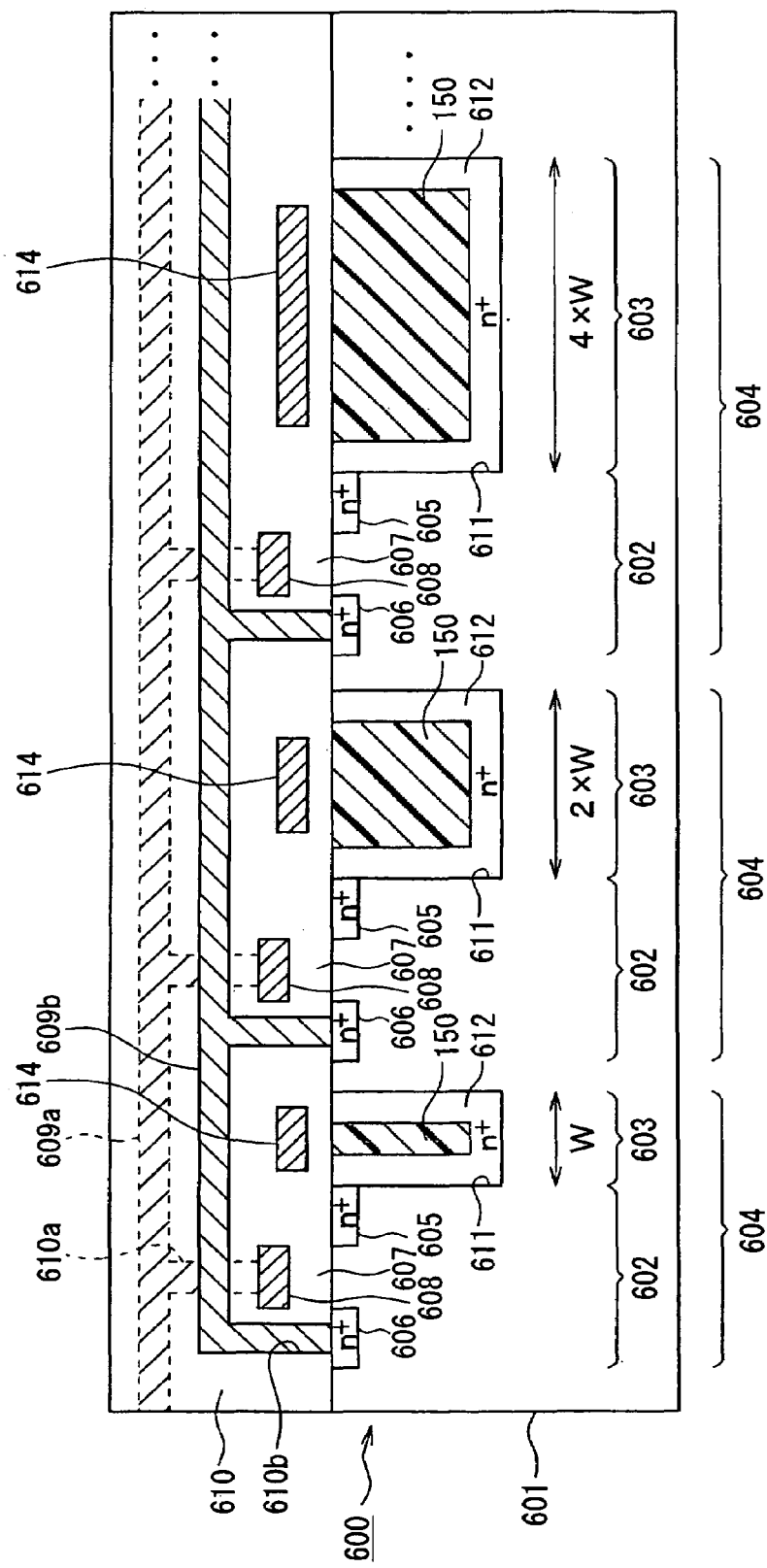
FIG. 12 is a partially enlarged cross sectional view showing a sensing portion of a humidity sensor according to a fourth embodiment of the present invention.

FIG. 12 shows a sectional structure of a sensing unit 600 of a humidity sensor, as a sensor apparatus to which a fourth embodiment mode of the present invention has been applied.

As indicated in FIG. 12, the sensing unit 600 of the humidity sensor has a plurality of memory cells 604 on a P type silicon substrate 601, each memory cell 604 being formed of an NMOS transistor 602 and a capacitor 603 as a pair.

The NMOS transistor 602 serves as a switching transistor and has a source region 605 and a drain region 606 which are formed in a surface layer portion of the silicon substrate 601 with an interval therebetween; and a gate electrode 608 formed on the surface of the silicon substrate 601 via a gate insulating film 607. As to this structure of the NMOS transistor 602, each memory cells 604 owns the same structure. That is, the gate electrode 608 of an NMOS transistor 602 equipped in each memory cells 604 is connected to a word line 609$a$, and the drain region 606 is connected to a bit line 609$b$.

It should be noted that both the word line 609$a$ and the bit line 609$b$ are formed on the gate electrode 608 via an interlayer insulating film 610, and electrically connected to the gate electrode 608 and the drain electrode 606 via contact holes 610$a$ and 610$b$ which are formed in the interlayer insulating film 610.

Using a trench 611 formed from the front surface to a predetermined depth of the silicon substrate 601, the capacitor 603 is constituted by an $n^+$ layer 612 formed on the inner wall of the trench 611, a humidity sensitive film 150 formed on the surface of the $n^+$ layer 612 so as to fill the trench 611, and an electrode 614 formed adjacent the humidity sensitive film 150.

Opening area of the trenches 611 is changed by making the widths thereof different in the respective memory cells 604. For example, with respect to a width "W" of the left-sided trench 611 as viewed in this drawing, the widths of the respective remaining trenches 611 are set to be successively doubled moving rightward in this drawing.

The n+ layer 612 has one end thereof contacted to the source region 605.

The humidity sensitive film 150 changes its dielectric constant "∈" in response to humidity in the atmosphere. As a result, the capacitance value of the capacitor 603 is determined based upon the dielectric constant "∈" contained in the humidity sensitive film 150.

The electrode 614 is arranged so as to face the humidity sensitive film 150 via an insulating film 607. Both electrodes which constitute the capacitor 603 are formed by this electrode 614 and the above-described humidity sensitive film 150.

In this case, the capacitance value "C" of the capacitor 603 is defined as follows:

$$C = \in \times S/d \quad \text{(Formula 1)}$$

Note that symbol "S" indicates an area in the capacitor 603, and generally corresponds to the area of a portion of the humidity sensitive film 150 which is located at the bottom plane of the trench 611. Also, symbol "d" represents an electrode interval in the capacitor 603, and corresponds to the depth of the humidity film 150.

As previously explained, as a consequence, the widths of the trenches 611 are changed in the respective memory cells 604, so that the capacitance values "C" of the capacitors 603 provided in the respective memory cells 604 own different values from each other.

Figure 13:
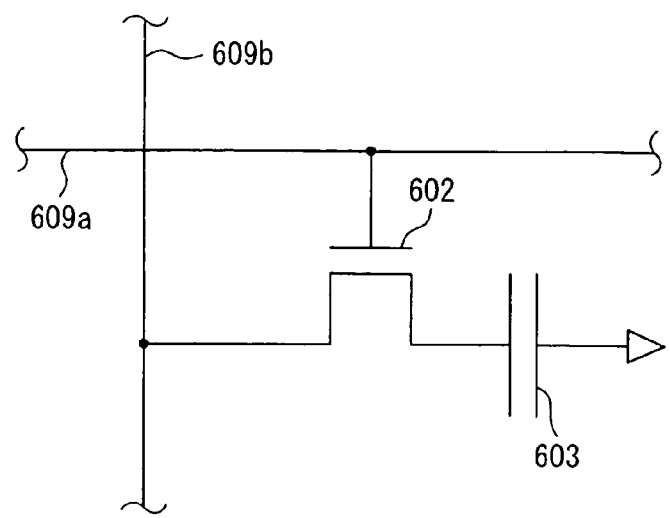
FIG. 13 is an equivalent circuit diagram showing one of memory cells in the sensing portion according to the fourth embodiment.

An equivalent circuit of each of the memory cells 604 in the humidity sensor of the above-explained structure is represented in FIG. 13.

Subsequently, FIG. 14 indicates a schematic structure of the sensor circuit of the humidity sensor.

Figure 14:
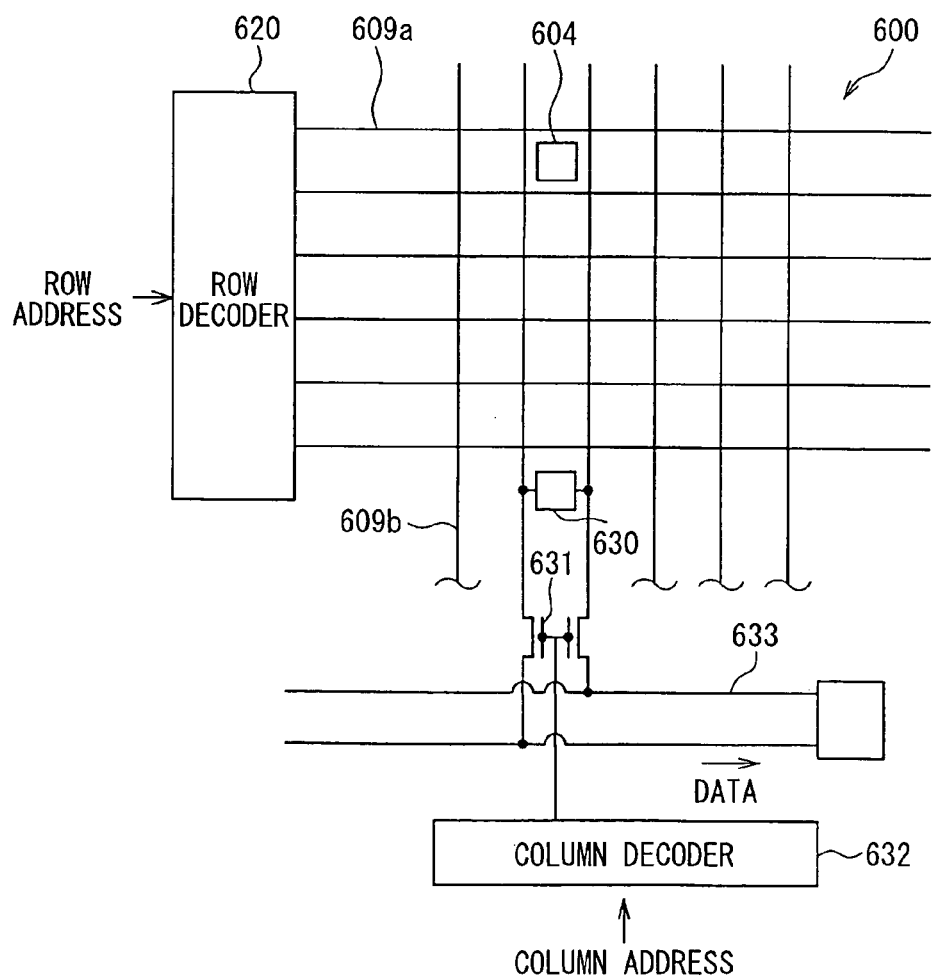
FIG. 14 is a schematic circuit diagram showing the humidity sensor according to the fourth embodiment.

As indicated in FIG. 14, a sensing unit 600 has a plurality of memory cells 604 arranged in a matrix form. It should be understood that each memory cell 604 shown in FIG. 13 is actually arranged in each section formed by being subdivided in the matrix shape in FIG. 14. However, in this drawing, this actual arrangement is omitted in order to simplify this drawing.

A row decoder 620 is provided to be connected to each word line 609a in this sensing unit 600. When a row address is inputted from a control unit (not shown) for driving the humidity sensor into the row decoder 620, this row decoder 620 applies a voltage to a corresponding word line 609a. As a result, a gate voltage is applied to the gate electrode 608 of the NMOS transistor 602 of such memory cell 604 that is electrically connected to the word line 609a designated by the row address out of the plural memory cells 604, and thus, the conductivity type of the surface layer portion of the silicon substrate 601, which is located under the gate electrode 608, is inverted so that the path between the source region 605 and the drain region 606 becomes conductive.

Also, a sense amplifier 630 and a column selection switch 631 are provided between the respective bit lines 609b in the sensing unit 600. The column selection switch 631 is constituted by, for example, an MOS transistor, and is driven by a column decoder 632. In other words, when a column address is inputted from a control unit (not shown) for driving the humidity sensor into this column decoder 632, the column decoder 632 adjusts the voltage which is applied to the column selection switch 631 in order that the column selection switch 631 corresponding to this inputted column address is turned ON. As a consequence, the column decoder 632 can control the connection condition between the bit line 609b and a data line 633 which is connected to the column selection switch 31.

The humidity sensor having the above-described structure has the plural memory cells 604 equipped with the plural capacitors 603, the capacitance values "C" of which are different from each other. As a result, in such a case that water contents responding to the humidity of the atmosphere are absorbed by the humidity sensitive film 150, even when the humidity within the atmosphere is the same, the capacitance values "C" of the plural capacitors 603 employed in the respective memory cells 604 become different from each other. That is to say, the capacitance values "C" which can be detected by the capacitors 603 in the respective memory cells 604 are changed.

As a consequence, if the threshold values of the plural memory cells 604 are made equal to each other, the writing conditions of the capacitors "C" of the respective memory cells 604 may become different from each other in response to the humidity in the atmosphere. In other words, the respective memory cells 604 are brought into the writing conditions when the capacitance values "C" of the capacitors 603 of the respective memory cells 604 become the predetermined values (threshold values). Then, since the capacitance value "C" of the capacitor 603 is expressed as the above-described formula 1, if the humidity is increased and the dielectric constant "∈" of the humidity sensitive film 150 is increased, then the capacitance value "C" of the capacitor 603 becomes large. This capacitance value "C" is defined with employing the area "S" and the dielectric constant "∈" of the capacitor 603 as variables, since the electrode intervals "d" of the capacitors 603 are made equal to each other in all of the plural memory cells 604. As a result, among the capacitors 603 provided in the respective memory cells 604, a capacitor 603 having a large area "S", namely, the one whose trench 611 has a large width owns a large capacitance value "C" even when the humidity is low, so that this capacitor 603 is brought into a writing condition. Conversely, among the capacitors 603 provided in the respective memory cells 604, a capacitor 603 having a small area "S", namely, the one whose trench 611 has a narrow width owns a small capacitance value "C" if the humidity is low, so that this capacitor 603 is brought into a non-writing condition.

As a consequence, the outputs of the respective memory cells 604 are substituted by "0" and "1", depending upon whether the present condition is brought into a non-writing condition, or a writing condition. That is, these outputs of the memory cells 604 become values in response to the humidity within the atmosphere.

Then, by reading out whether the respective memory cells 604 are in the non-writing condition or the writing condition, through respective data lines for the respective memory cells 604, it is possible to obtain the sensor output responding to the humidity as a digital value.

As explained above, in accordance with the humidity sensor of this embodiment mode, the humidity sensor can produce the digital outputs without requiring the A/D converter. As a result, it is possible to avoid that the circuit arrangement of the humidity sensor becomes complex, and the humidity sensor can be made compact.

(Fifth Embodiment)

Figure 15:
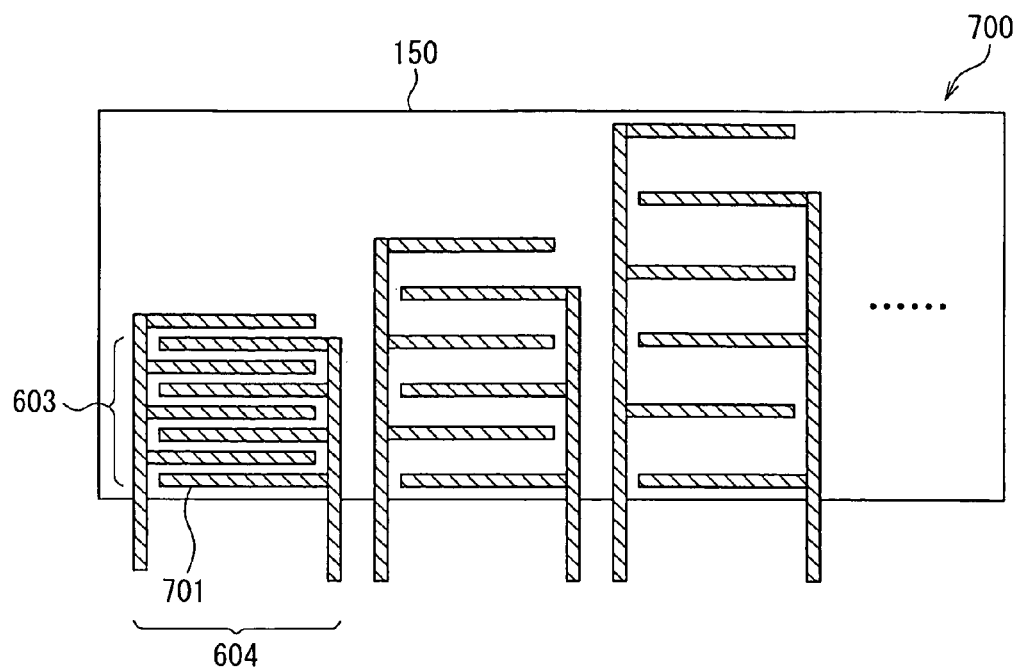
FIG. 15 is a plan view showing a layout of a sensing portion of a humidity sensor according to a fifth embodiment of the present invention.
Figure 16:
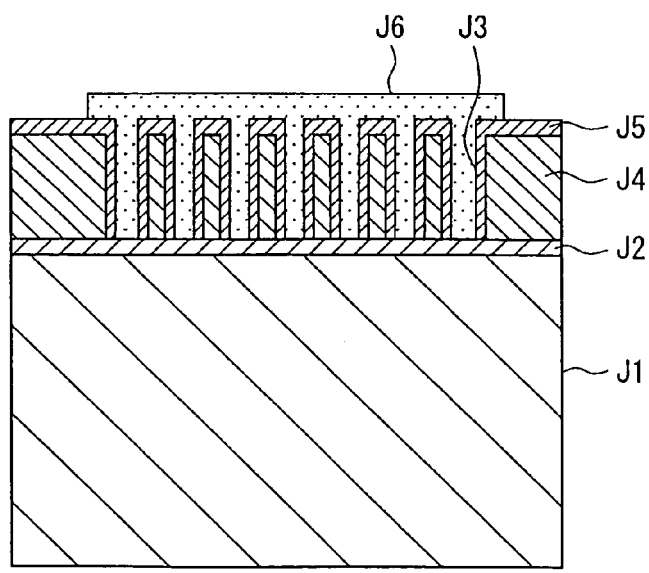
FIG. 16 is a partially enlarged cross sectional view showing a sensing portion of a humidity sensor as a prototype according to a comparison of the fourth embodiment.

Next, a description is made of a fifth embodiment mode of the present invention. FIG. 15 shows a layout structure of a sensing unit 700 employed in a humidity sensor to which the fifth embodiment mode of the present invention is applied.

As indicated in this drawing, in this fifth embodiment mode, each of capacitors 603 is constituted by a plurality of comb-teeth-shaped electrodes 701. It should also be noted that although only one capacitor 603 within a memory cell 604 is illustrated, switching transistors similar to those of the fourth embodiment mode are actually equipped in each of the memory cells 604.

Intervals among the plural comb-teeth-shaped electrodes 701 are set to be successively double moving rightward in this drawing. Then, humidity sensitive films 150 are provided over the entire surface of the sensing unit 700 equipped with such comb-teeth-shaped electrodes 701 so as to fill the spaces among the respective comb-teeth-shaped electrodes 701.

Similar to the fourth embodiment mode, in such a type of humidity sensor that the capacitors 603 are formed by such comb-teeth-shaped electrodes 701, the capacitance values "C" of the capacitors 603 are changed in response to the intervals among these comb-teeth-shaped electrodes 701. As a result, similar to the fourth embodiment mode, the outputs of the humidity sensor can be digitally represented. As a consequence, an effect similar to that of the first embodiment mode can be obtained.

In the above-described fourth and fifth embodiment modes, by changing the widths of the trenches 611, the opening areas of the trenches 611 are changed so as to change the capacitance values "C" of the capacitors 603. Alternatively, even when the depths of the trenches 611, namely the sizes thereof along the vertical direction (as viewed in FIG. 12) are changed every memory cell 604, a similar effect to that of the fourth embodiment mode may be achieved. In this alternative case, however, since the lengths of the respective trenches 611 along the depth direction are different from each other, the size of the semiconductor substrate 601 used to construct the humidity sensor must be increased. As a consequence, it is preferable to employ the structure as explained in the above-described embodiment modes.

Also, in the above-described fourth and fifth embodiment modes, the widths of the trenches 611 are successively doubled. Alternatively, if the widths of the trenches 611 are set to be gradually increased, then it becomes possible the humidity changing gradually. In this alternative case, outputs of the humidity sensor may be approximated to linear outputs.

Also, the above-explained fourth and fifth embodiment modes have been described with the case that the NMOS transistors 602 are employed, and the n$^+$ type layers 612 are formed in the trenches 611, namely the case the first conductivity type is n type, and the second conductivity type is p type. This merely implies one example. That is, the present invention may be similarly applied to such a reverse structure that the first conductivity type is selected to be a "p" type, and the second conductivity type is selected to be an "n" type, the conductivity types thereof being reversed to those of the respective embodiment modes.

Furthermore, unlike the embodiment modes described above, the widths of the trenches 611 constituting the respective capacitors 603 may be made equal to each other. In this alternative case, as to all of the capacitors 603 of the plural memory cells 604, the behavior as to whether or not the present condition is brought into the writing condition may be coincident with each other at the same humidity. As a result, such alternative structure may be applied as an ON/OFF switch capable of detecting that humidity becomes a predetermined threshold value.

While the invention has been described with reference to preferred embodiments thereof, it is to be understood that the invention is not limited to the preferred embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. Sensor equipment for generating an output in accordance with a physical quantity as a detection object, the equipment comprising:
   a decoder; and
   a semiconductor substrate including a plurality of memory cells, each of which includes a transistor for switching and a capacitor, wherein
   the transistor in each memory cell includes a source region, a drain region, and a gate electrode,
   the source region and the drain region have a first conductive type,
   the gate electrode is disposed in an insulation layer such that the gate electrode is between the the source region and the drain region and is also adjacent the semiconductor substrate,
   the capacitor in each memory cell includes a trench, a semiconductor region, a dielectric film, and a capacitance electrode,
   the trench is disposed in the semiconductor substrate,
   the semiconductor region having the first conductive type is disposed in the trench, and is connected to the source region,
   the dielectric film has a dielectric constant that changes in accordance with the physical quantity,
   the dielectric film is embedded in the semiconductor region in the trench in such a manner that the dielectric film is disposed on a surface of the semiconductor region,
   the capacitance electrode is disposed on a surface of the dielectric film through an insulation film in such a manner that the capacitance electrode faces the trench,
   the trench in each memory cell has a width which is different for each memory cell so that the opening area of the trench is different in each memory cell, and
   the decoder is capable of detecting whether each memory cell is in either a written state or in an unwritten state, and outputting the state of each memory cell.

2. The equipment according to claim 1, wherein the width of the trenches increases by a factor of $2^N$, where N represents whole number.

3. The equipment according to claim 1, wherein the dielectric film is a humidity sensitive film having a dielectric constant which changes in accordance with the humidity in the atmosphere.

4. Sensor equipment for generating an output in accordance with a physical quantity as a detection object, the equipment comprising:
   a decoder; and
   a semiconductor substrate including a plurality of memory cells, each of which includes a transistor for switching and a capacitor, wherein
   the transistor includes a source region, a drain region, and a gate electrode,
   the source region and the drain region have a first conductive type, the gate electrode is disposed in an insulation layer such that the gate electrode is between the source region and the drain region and is also adjacent to the semiconductor substrate, the capacitor includes a pair of comb-teeth electrodes and a dielectric film, the comb-teeth electrodes are disposed on the semiconductor substrate, the dielectric film is capable of changing dielectric constant of the dielectric film in accordance with the physical quantity, the dielectric film fills the spaces between the comb-teeth electrodes, the comb-teeth electrodes in each memory cell are separated from each other by a predetermined distance, the predetermined distance is different for each memory cell, and the decoder is capable of detecting whether each memory cell is in either a written state or in an unwritten state, and outputting the state of each memory cell.

5. The equipment according to claim 4, wherein the differences in the predetermined distances increases by a factor of $2^N$, where N is a whole number.

6. The equipment according to claim 4, wherein the dielectric film is a humidity sensitive film having a dielectric constant which changes in accordance with the humidity in the atmosphere.

* * * * *

UNITED STATES PATENT AND TRADEMARK OFFICE
CERTIFICATE OF CORRECTION

| | | |
|---|---|---|
| PATENT NO. | : 7,181,966 B2 | Page 1 of 1 |
| APPLICATION NO. | : 11/220543 | |
| DATED | : February 27, 2007 | |
| INVENTOR(S) | : Toshiki Isogai, Michitaka Hayashi and Toshikazu Itakura | |

It is certified that error appears in the above-identified patent and that said Letters Patent is hereby corrected as shown below:

Title Page

Correct the named inventors (item 75)

Item (75) should read,
  (75) Inventors:

Toshiki ISOGAI, Nagoya (JP);
        Michitaka HAYASHI, Nagoya (JP);
        Toshikazu ITAKURA, Toyota (JP)

Signed and Sealed this

Nineteenth Day of June, 2007

JON W. DUDAS
*Director of the United States Patent and Trademark Office*